US009738906B2

(12) United States Patent
Eto et al.

(10) Patent No.: US 9,738,906 B2
(45) Date of Patent: Aug. 22, 2017

(54) METHOD FOR PRODUCING POLYPLOIDIZED MEGAKARYOCYTE AND PLATELETS

(75) Inventors: Koji Eto, Kyoto (JP); Hiromitsu Nakauchi, Tokyo (JP); Naoya Takayama, Kyoto (JP); Sou Nakamura, Tokyo (JP)

(73) Assignee: The University of Tokyo, Tokyo (JP)

( * ) Notice: Subject to any disclaimer, the term of this patent is extended or adjusted under 35 U.S.C. 154(b) by 65 days.

(21) Appl. No.: 14/117,465

(22) PCT Filed: May 11, 2012

(86) PCT No.: PCT/JP2012/062217
§ 371 (c)(1),
(2), (4) Date: Jan. 13, 2014

(87) PCT Pub. No.: WO2012/157586
PCT Pub. Date: Nov. 22, 2012

(65) Prior Publication Data
US 2014/0127815 A1 May 8, 2014

(30) Foreign Application Priority Data

May 13, 2011 (JP) .................................. 2011-108253

(51) Int. Cl.
C12N 5/078 (2010.01)
C12N 15/85 (2006.01)
A61K 35/19 (2015.01)

(52) U.S. Cl.
CPC .............. *C12N 15/85* (2013.01); *A61K 35/19* (2013.01); *C12N 5/0644* (2013.01); *C12N 2501/165* (2013.01); *C12N 2501/48* (2013.01); *C12N 2506/02* (2013.01)

(58) Field of Classification Search
CPC ............................ C12N 15/85; C12N 5/0644
See application file for complete search history.

(56) References Cited

U.S. PATENT DOCUMENTS

| 9,200,254 B2* | 12/2015 | Eto ....................... C12N 5/0644 |
| 2010/0197016 A1 | 8/2010 | Nakauchi et al. |
| 2011/0053267 A1 | 3/2011 | Nakauchi et al. |
| 2012/0238020 A1* | 9/2012 | Mitchell et al. ............... 435/377 |
| 2012/0238023 A1* | 9/2012 | Eto et al. ....................... 435/467 |

FOREIGN PATENT DOCUMENTS

| JP | 2009-213645 | * | 9/2009 | ............... C12N 5/06 |
| JP | 2009-213645 | * | 10/2010 | |
| JP | WO/2011/034073 | * | 3/2011 | |
| WO | 2008/041370 A1 | | 4/2008 | |
| WO | 2009/122747 A1 | | 10/2009 | |
| WO | 2011/034073 A1 | | 3/2011 | |

OTHER PUBLICATIONS

Kaluzhny et al. (Blood. 2002; 100: 1670-1678).*
Sanz et al (Experimental Hematology. 2001. 29: 728-735).*
Michels et al. (International Journal of Cell Biology. 2013. article 705294, pp. 1-10).*
Boyer et al. (Journal of Immunological Methods. 2008; 332:82-91).*
Oguro et al (JEM. 2006. 203(10): 2247-2253).*
Serrano et al. "Role of the INK4a Locus in Tumor Suppression and Cell Mortality"; Cell 1996. 85: 27. PMID: 8620534.*
Chang et al. (Blood. 2007; 109:4229-4236).*
Takayama et al., "Generation of functional platelets from human embryonic stem cells in vitro via ES-sacs, VEGF-promoted structures that concentrate hematopoietic progenitors," Blood, 111: 5298-5306 (2008).
Lordier et al., "Megakaryocyte endomitosis is a failure of late cytokinesis related to defects in the contractile ring and Rho/Rock signaling," Blood, 112: 3164-3174 (2008).
Schweinfurth et al., "Valproic acid and all trans retinoic acid differentially induce megakaryopiesis and platelet-like particle formation from the megakaryoblastic cell line MEG-01," Platelets, 21: 648-657 (2010).
Fuhrken et al., "Tumor Suppressor Protein p53 Regulates Megakaryocytic Polyploidization and Apoptosis," Journal of Biological Chemistry, 283: 15589-15600 (2008).
Proulx et al., "Increased Megakaryopoiesis in Cultures of CD34-Enriched Cord Blood Cells Maintained at 39° C.," Biotechnology and Bioengineering, 88: 575-580 (2004).
Terui et al., "Bcl-x is a regulatory factor of apoptosis and differentiation in megakaryocytic lineage cells," Experimental Hematology, 26: 236-244 (1998).
Kaluzhny et al., "BclxL overexpression in megakaryocytes leads to impaired platelet fragmentation," Blood, 100: 1670-1678 (2002).
International Search Report issued in corresponding International Patent Application No. PCT/JP2012/062217 dated Jul. 17, 2012.
Zhang et al., "Early down-regulation of Bcl-xL expression during megakaryocytic differentiation of thrombopoietin-induced CD34+ bone marrow cells in essential thrombocythemia," Haematologica, 89: 1199-1206 (2004).
Sanz et al., "Antiapoptotic protein Bcl-xL is up-regulated during megakaryocytic differentiation of CD34+ progenitors but is absent from senescent megakaryocytes," Experimental Hematology, 29: 728-735 (2001).
Zhao et al., "The clock gene Per2 is required for normal platelet formation and function," Thrombosis Research, 127: 122-130 (2011).

(Continued)

Primary Examiner — Scott Long
(74) Attorney, Agent, or Firm — Morgan, Lewis & Bockius LLP

(57) ABSTRACT

An object of the present invention is to provide a method of promoting polyploidization of megakaryocytes and thereby producing highly polyploidized megakaryocytes, a method of efficiently producing platelets from polyploidized megakaryocytes, and the like. The present invention provides a method of producing polyploidized megakaryocytes comprising a step of forcing expression of an apoptosis suppressor gene in megakaryocytes before polyploidization and culturing the resulting cells.

17 Claims, 28 Drawing Sheets

(56) References Cited

OTHER PUBLICATIONS

Takayama et al., "Transient activation of c-MYC expression is critical for efficient platelet generation from human induced pluripotent stem cells," Journal of Experimental Medicine, 207: 2817-2830 (2010).

Nakamura et al., "Expandable Megakaryocyte Cell Lines Enable Clinically Applicable Generation of Platelets from Human Induced Pluripotent Stem Cells," Cell Stem Cell, 14: 535-548 (2014).

* cited by examiner

A

B

A

BLEBBISTATIN

B

METHOD FOR PRODUCING POLYPLOIDIZED MEGAKARYOCYTE AND PLATELETS

SEQUENCE LISTING SUBMISSION VIA EFS-WEB

A computer readable text file, entitled "SequenceListing.txt," created on or about Nov. 12, 2013 with a file size of about 5 kb contains the sequence listing for this application and is hereby incorporated by reference in its entirety.

TECHNICAL FIELD

The present invention relates to a method for efficiently polyploidizing megakaryocytes before polyploidization, a method for producing platelets from such megakaryocytes, and the like.

BACKGROUND ART

Large numbers of blood cells are required for the treatment of blood-related diseases or surgical treatments. Among blood cells, a platelet which is a cell indispensable for blood coagulation and hemostasis is one of particularly important blood cells. The platelet is in high demand in leukemia, bone marrow transplantation, anticancer treatment, and the like so that necessity of stable supply of it is high. The platelet has so far been supplied stably by, as well as a method of collecting it from the blood donated by donors, a method of administering a drug having a TPO-like (mimetic) structure, a method of differentiating megakaryocytes from the cord blood or bone marrow cells, or the like method. Recently, there has been developed a technology of inducing in vitro differentiation of pluripotent stem cells such as ES cells or iPS cells to prepare blood cells such as platelets.

The present inventors have established a technology of inducing differentiation of megakaryocytes and platelets from human ES cells and shown effectiveness of ES cells as a source of platelets (Patent Document 1 and Non-patent Document 1). In addition, the present inventors have established a method for preparing megakaryocytes and platelets from iPS cells and have enabled dissolution of the problem of compatibility of a human leukocyte antigen (HLA) which inevitably occurred in transfusion of platelets derived from ES cells (Patent Document 2).

Further, with a view to overcoming the problem of the amount of platelets and the like prepared from stem cells, the present inventors have found a method of establishing and thereby preparing an immortalized megakaryocyte progenitor cell line from the stem cells and thus, have developed an important technology for in vitro preparation of a large amount of platelets and the like (Patent Document 3).

In vivo, megakaryocytes form pseudopodial formation called proplatelets (platelet progenitors), fractionate their cytoplasm, and release platelets. Polyploidization of megakaryocytes is thought to occur by endomitosis until they release platelets. Endomitosis of megakaryocytes is multipolar mitosis not accompanied with cleavage furrow formation and spindle extension and caused by abnormal karyokinesis and cytoplasm mitosis. As a result of endomitosis, cells containing several segmented nuclei are formed. Polyploidization of megakaryocytes is induced by repetition of such endomitosis.

Many study results have been reported to date on polyploidization of megakaryocytes. Lodier, et al. have elucidated (Non-patent Document 1) that in endomitosis of megakaryocytes, localization of nonmuscle cell myosin II in a contractile ring has not been recognized in spite of formation of cleavage furrow and defects occur in contractile ring formation and spindle extension. It has been shown that such abnormalities in contractile ring or spindle extension become more marked by inhibiting RhoA and Rock activities (Non-patent Document 2). RhoA accumulates at the cleavage furrow and promotes activation of some effector factors including Rho kinase (Rock), citron kinase, LIM kinase, and mDia/formins. These results suggest that by inhibiting the activities of factors such as RhoA and Rock involved in formation of a contractile ring, endomitosis of megakaryocytes is promoted. There is also a report that when a Rho signal positioned downstream of integrin alpha2/beta1 is reinforced, formation of proplatelets of immature megakaryocytes before polyploidization is inhibited.

It is reported that all trans retinoic acid (ATRA), a transcription factor and valproic acid which is known as a histone deacetylase inhibitor are involved in differentiation of megakaryocytes. Schweinfurth, et al. have found that treatment of immature megakaryocytes with all trans retinoic acid or valproic acid promotes polyploidization (Non-patent Document 3). Further, it is reported that polyploidization of megakaryocytes is promoted when p53, a cancer suppressor gene product is knocked down (Non-patent Document 4).

It has also been shown that as an influence on a differentiation procedure of megakaryocytes, culturing immature megakaryocytes at 39° C., temperature higher than conventional culturing temperature, promotes induction to polyploidized mature megakaryocytes and formation of proplatelets (Non-patent Document 5).

CITATION LIST

Patent Documents

Patent Document 1: WO2008/041370
Patent Document 2: WO2009/122747
Patent Document 3: WO2011/034073

Non-Patent Documents

Non-patent Document 1: Takayama, et al., Blood, 111: 5298-5306 2008
Non-patent Document 2: Lordier, et al., Blood, 112: 3164-3174 2009
Non-patent Document 3: Schweinfurth, et al., Platelets, 21: 648-657 2010
Non-patent Document 4: Fuhrken, et al., J. Biol. Chem., 283: 15589-15600 2008
Non-patent Document 5: Proulx et al., Biotechnol. Bioeng., 88: 675-680 2004

SUMMARY OF THE INVENTION

Problem to be Solved by the Invention

Finding that the amount of functional platelets (platelets having in vivo activities such as hemostatic action and characterized as CD42b+) available from megakaryocytes whose "polyploidization" has not proceeded sufficiently is too small to develop clinical application, the present inventors thought that polyploidization of megakaryocytes should be promoted in order to efficiently produce functional platelets in vitro.

An object of the present invention is therefore to provide a method of promoting polyploidization of megakaryocytes and thereby preparing more polyploidized megakaryocytes, a method of efficiently producing platelets from polyploidized megakaryocytes, and the like.

Means for Solving the Problem

With the foregoing problem in view, the present inventors tried to promote polyploidization of megakaryocytes which have been prepared from pluripotent stem cells (ES cells, iPS cells, and the like) and whose polyploidization has not proceeded sufficiently. First, the present inventors made this trial with the immortalized megakaryocytic progenitor cell line (refer to Patent Document 3) prepared from pluripotent stem cells developed by themselves. This immortalized megakaryocytic progenitor cell line is the one which is imparted with enhanced proliferative potential and is established (immortalized) by inducing expression of an oncogene such as MYC or a gene such as BMI1 in the megakaryocyte progenitor cells derived from pluripotent stem cells.

With a view to promoting polyploidization with this immortalized megakaryocytic progenitor cell line, the present inventors have succeeded in efficiently promoting polyploidization by forcing expression of an apoptosis suppressor gene when suppression of expression of an oncogene and a polycomb gene is conducted.

The present inventors have also confirmed that as well as forced expression of an apoptosis suppressor gene, inhibiting expression or function of a p53 gene product further increases efficiency of polyploidization. They have further confirmed that subjecting the megakaryocytic progenitor cell line to treatment with an ROCK (Rho-associated coiled-coil forming kinase/Rho associated kinase) inhibitor or an HADC inhibitor, to culture at 39° C., and the like is also effective for inducing polyploidization. Moreover, they have found that treatment with an actomyosin complex (complex of actin and myosin) function inhibitor highly promotes polyploidization.

They have found that highly polyploidized megakaryocytes produced by the present invention contain megakaryocytes of 4N or 8N or greater at a ratio higher than that of known ones and at the same time, contain such cells at a ratio much higher than that of mature megakaryocytes produced in vivo.

Further, the present inventors have found that in sufficiently polyploidized mature megakaryocytes, the number of platelets produced from one megakaryocyte shows a drastic increase by suppressing the forced expression of an apoptosis suppressor gene. In addition, they have confirmed that the platelet production efficiency can be further increased by culturing on a medium added with an ROCK inhibitor. After studying the optimum conditions for culturing period, culturing temperature, and the like, they have completed the present invention.

The present invention relates to:

[1] a method of producing polyploidized megakaryocytes, including a step of forcing expression of an apoptosis suppressor gene in megakaryocytes before polyploidization and culturing the cells;

[2] the method described above in [1], wherein the apoptosis suppressor gene is a BCL-XL gene;

[3] the method described above in [1] or [2], wherein in the culturing step, expression or function of a p53 gene product is inhibited;

[4] the method described above in any one of [1] to [3], wherein in the culturing step, the megakaryocytes before polyploidization are subjected to at least one of the following (a) to (c):

(a) treatment with an actomyosin complex function inhibitor;

(b) treatment with an ROCK inhibitor; and (c) treatment with an HDAC inhibitor;

[5] the method as described above in [4], wherein the ROCK inhibitor is Y27632; the HDAC inhibitor is valproic acid; and the actomyosin complex function inhibitor is blebbistatin;

[6] the method described above in any one of [1] to [5], wherein the culturing step is conducted at a temperature higher than 37° C.;

[7] the method described above in any one of [1] to [6], wherein the megakaryocytes before polyploidization are obtained by a step of forcing expression of an oncogene and any of the following genes (i) to (iii) in the cells at any differentiation stage from hematopoietic progenitor cells to megakaryocytes before polyploidization:

(i) a gene suppressing expression of a p16 gene or a p19 gene;

(ii) a gene suppressing expression of an Ink4a/Arf gene; and (iii) a polycomb gene; and culturing and proliferating the cells;

[8] the method described above in [7], wherein a c-MYC gene is used as the oncogene and BMI1 is used as the any of the genes (i) to (iii);

[9] the method described above in [7] or [8], wherein the hematopoietic progenitor cells are derived from cells selected from the group consisting of iPS cells, ES cells, hematopoietic stem cells derived from cord blood, bone marrow blood, or peripheral blood, and hematopoietic stem cells;

[10] a blood cell composition containing the polyploidized megakaryocytes produced by the method described above in any one of [1] to [9];

[11] a method of producing a platelet, including:

a step of obtaining polyploidized megakaryocytes by using the method described above in any one of [1] to [9] and culturing the cells; and a step of collecting a platelet from the culture of the polyploidized megakaryocytes;

[12] the method described above in [11], wherein the step of culturing the polyploidized megakaryocytes is conducted while suppressing the expression of the apoptosis suppressor gene that has been forcibly expressed or after the apoptosis suppressor gene is removed from the cells;

[13] the method described above in [11] or [12], wherein the step of culturing the polyploidized megakaryocytes is conducted in the absence of a serum and/or in the absence of a feeder cell;

[14] the method described above in any one of [11] to [13], wherein the step of culturing the polyploidized megakaryocytes is conducted from one day to 15 days;

[15] the method described in any one of [11] to [14], wherein the step of culturing the polyploidized megakaryocytes is conducted at 37° C.;

[16] the method described above in any one of [11] to [15], wherein in the step of culturing the polyploidized megakaryocytes, an ROCK inhibitor and/or an actomyosin complex function inhibitor is added to a medium;

[17] the method described above in [16], wherein the ROCK inhibitor is Y27632 and the actomyosin complex function inhibitor is blebbistatin;

[18] a platelet produced by the method described in any of [11] to [17]; and

[19] a blood product containing the platelet described above in [18].

Effect of the Invention

The present invention makes it possible to artificially promote polyploidization of megakaryocytes. In particular, the present invention is effective also for promotion of polyploidization of megakaryocytes prepared in vitro as previously reported, and the invention makes it possible to provide megakaryocytes (for example, a megakaryocyte population having megakaryocytes of 4N or greater at a high ratio) whose polyploidization level has proceeded more than megakaryocytes available in vivo.

Further, the present invention makes it possible to markedly increase the number of platelets produced per polyploidized megakaryocyte.

It becomes possible to drastically decrease the time necessary for producing platelets from stem cells and then to conduct mass production of the platelets by inducing megakaryocytes before polyploidization from stem cells, proliferating the megakaryocytes before polyploidization using, for example, the method described in Patent Document 3, and polyploidizing the megakaryocytes before polyploidization to produce platelets according to the method of the present invention. The platelets obtained as described above are CD42b positive and largely contribute to clinical application.

BMI1 in megakaryocytes (by culturing in the presence of doxycycline and in the absence of estradiol), adding blebbistatin (10 µg/ml), a myosin heavy chain IIA/B ATPase inhibitor, and culturing for 7 days. A shows flow cytometry histograms of cells (−) to which blebbistatin had not been added and of cells (+) to which blebbistatin (10 µg/ml) had been added, wherein these cells were stained with a nuclear stain Hoechst, and then CD41a, a megakaryocyte marker was stained with an anti-CD41a antibody. B is a graph showing the results of A.

Figure 12:
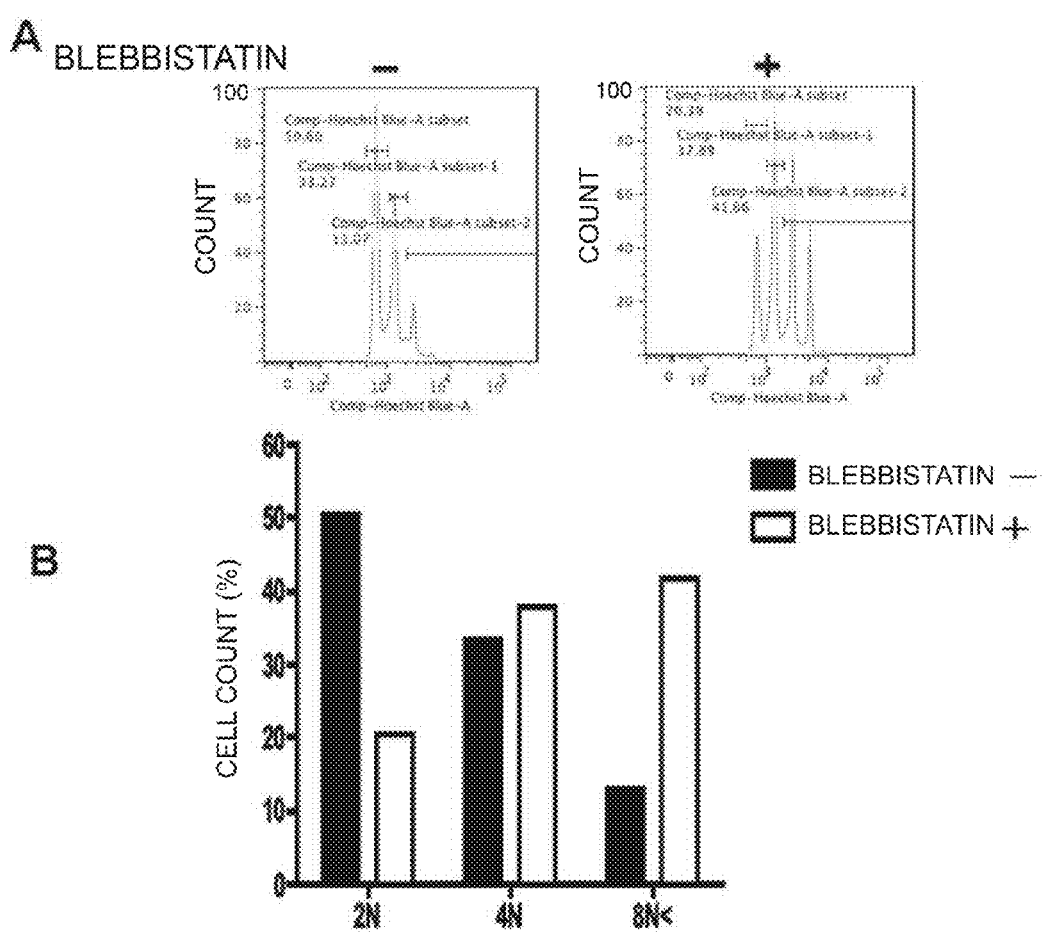

FIG. 12 Influence, on polyploidization of megakaryocytes, of blebbistatin treatment used in combination with the other treatments. The degree of polyploidization of CD41a+ cells were studied after suppressing the expression of MYC/BMI1 in megakaryocytes, inducing expression of BCL-XL in the presence of Y27632 (10 µM) and valproic acid (0.5 mM), knocking down a p53 gene, adding blebbistatin (10 µg/ml), and culturing at 39° C. for 7 days. A shows flow cytometry histograms of each of cells (−) not treated with blebbistatin and cells (+) treated with blebbistatin, wherein these cells were stained with a nuclear stain, Hoechst, and then a CD41a, a megakaryocyte marker was stained with an anti-CD41a antibody. B is a graph showing the results of A.

Figure 13:
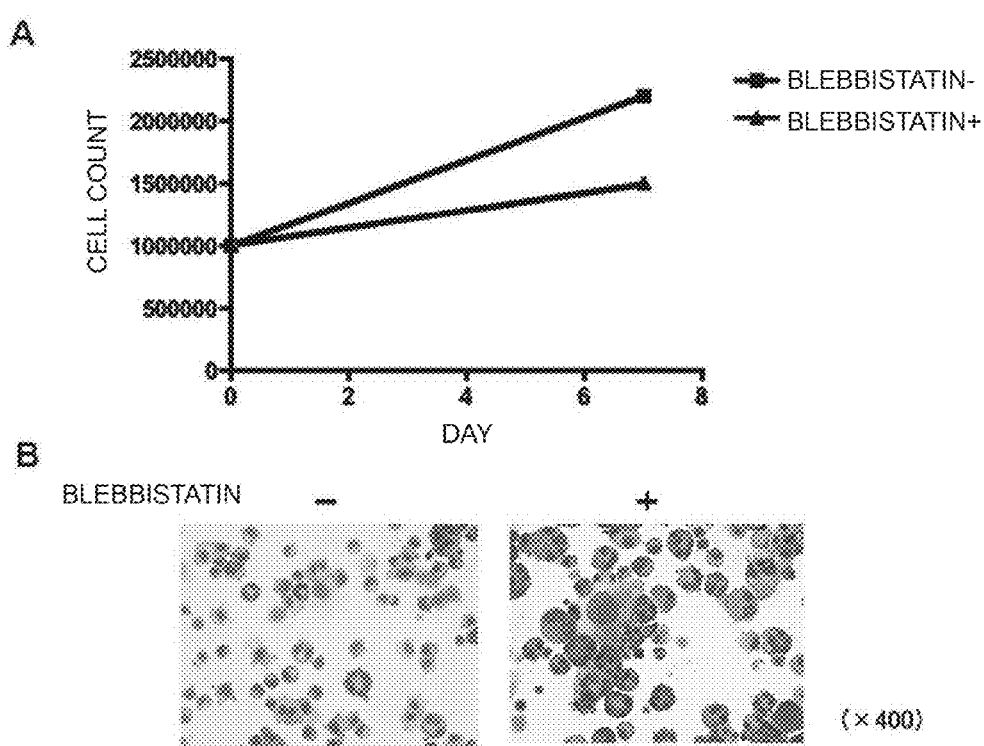

FIG. 13 Growth curve of cells subjected to blebbistatin treatment in combination with the other treatments. A change in the number of the following cells was graphed (A) as a function of culturing days: cells (CD41a+) treated with blebbistatin (CD41a+) (▲) and cells (CD41a+) not treated with blebbistatin (■), each after expression of MYC/BMI1 in megakaryocytes was suppressed, BCL-XL was expressed in the presence of Y27632 (10 µM) and valproic acid (0.5 mM), and a p53 gene was knocked down. Micrographs of these cells are shown in B.

Figure 14:
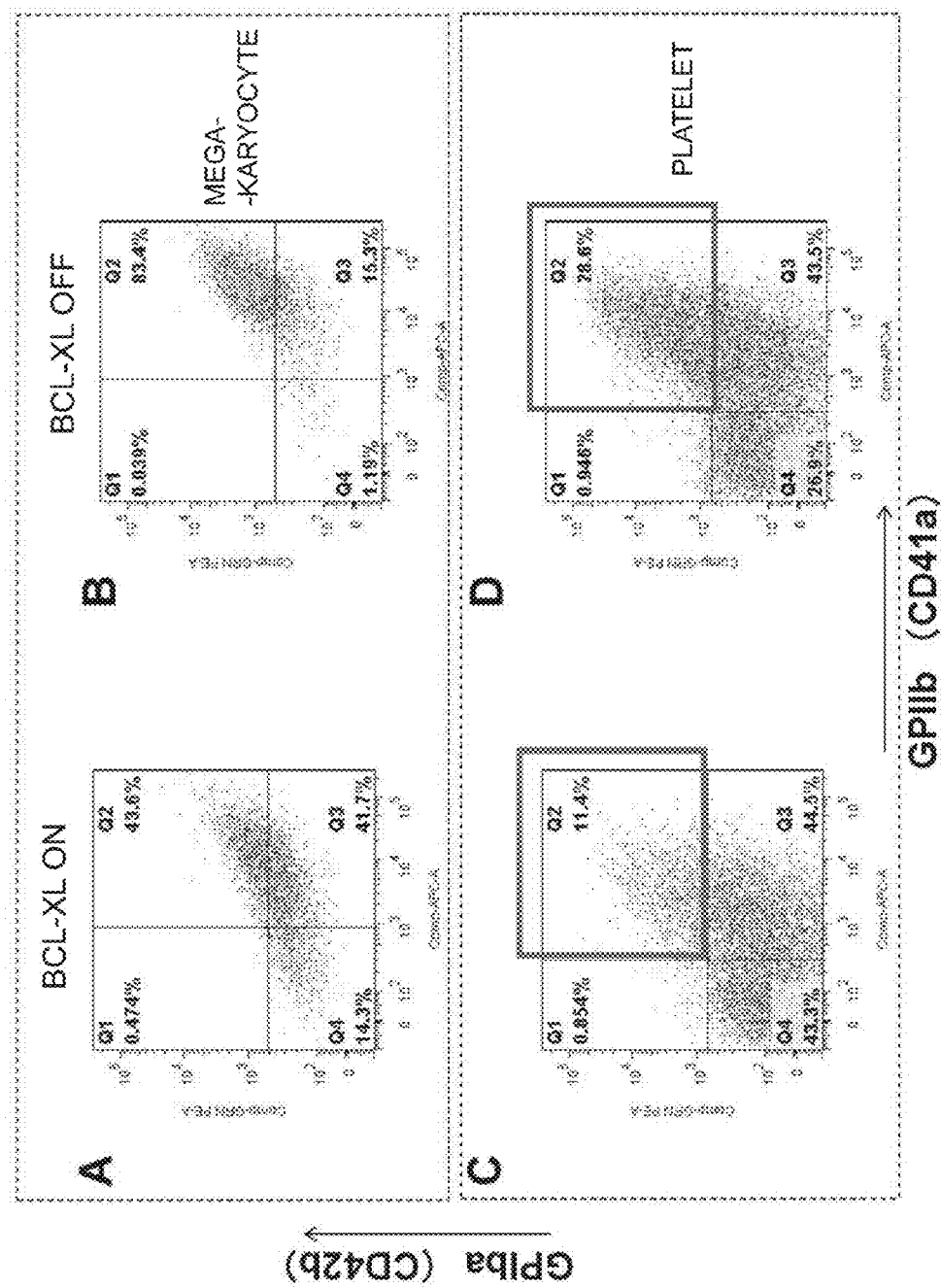

FIG. 14 It shows the results of studying expression of CD41a and CD42b in megakaryocytes and platelets in both cases where expression of BL-XL was suppressed and where it was not suppressed during a platelet release stage.

Figure 15:
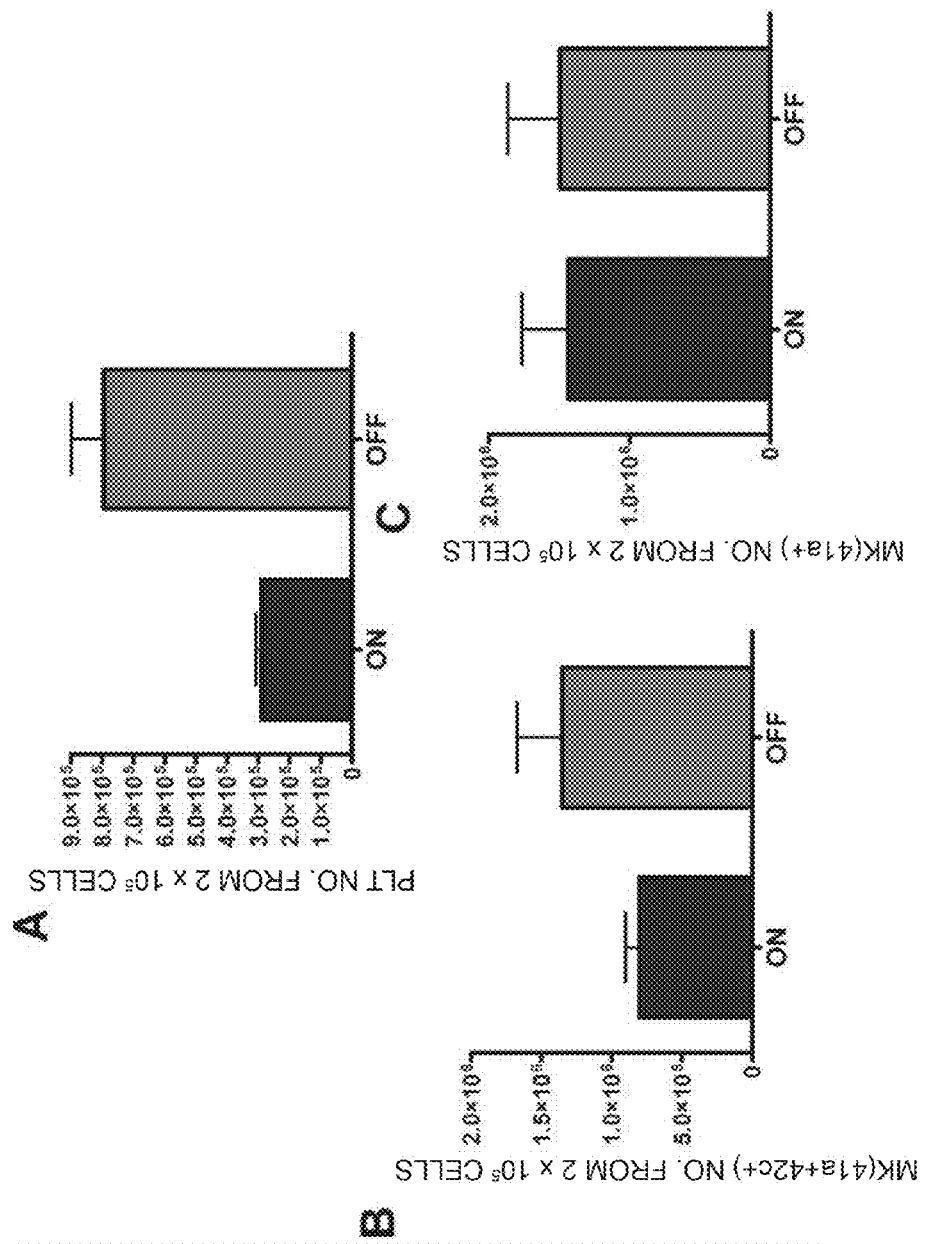

FIG. 15 It shows cell counts measured at the time of ON/OFF of BCL-XL expression based on the results of FIG. 14. A shows the number of CD42b-positive platelets, B shows the number of CD41a-positive/CD42b-positive megakaryocytes, and C shows the number of CD41a-positive megakaryocytes.

Figure 16:
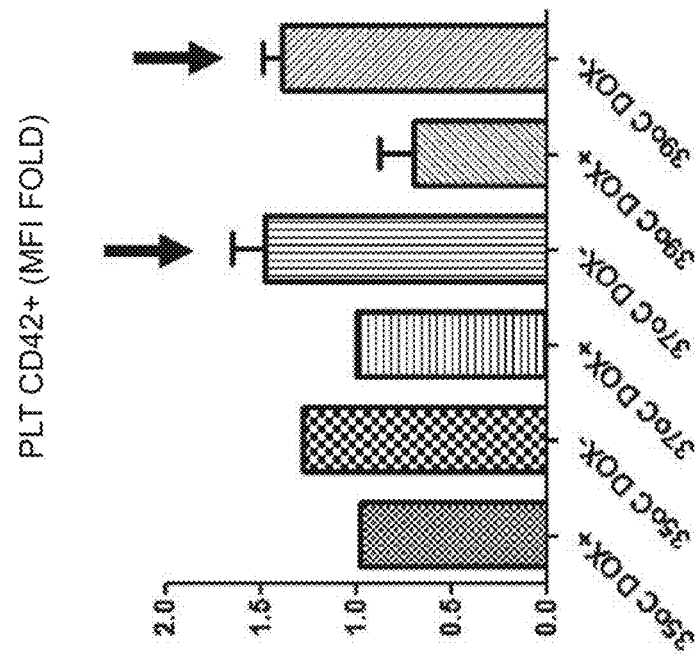
Figure 16:
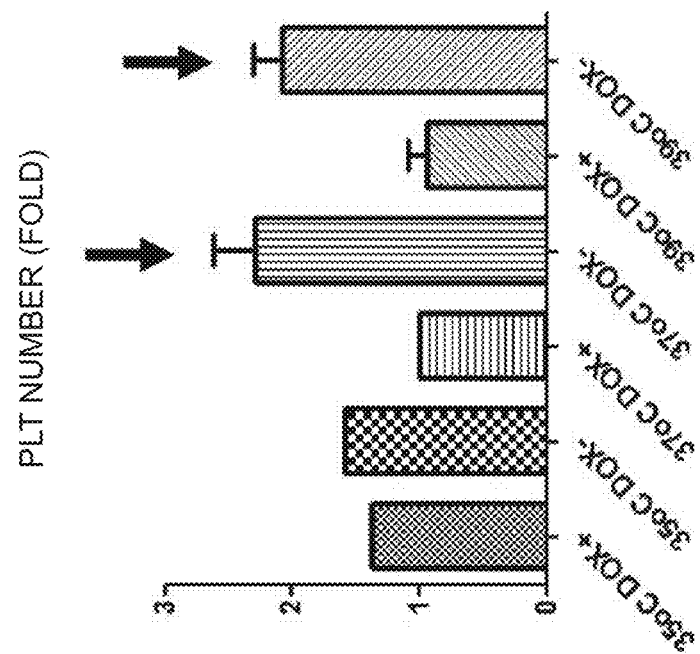

FIG. 16 It shows the results of studying the influence of culturing temperatures set at 35° C., 37° C., and 39° C. on the number of platelets in both cases where expression of BCL-XL was suppressed and where it was not suppressed during a platelet release stage.

Figure 17:
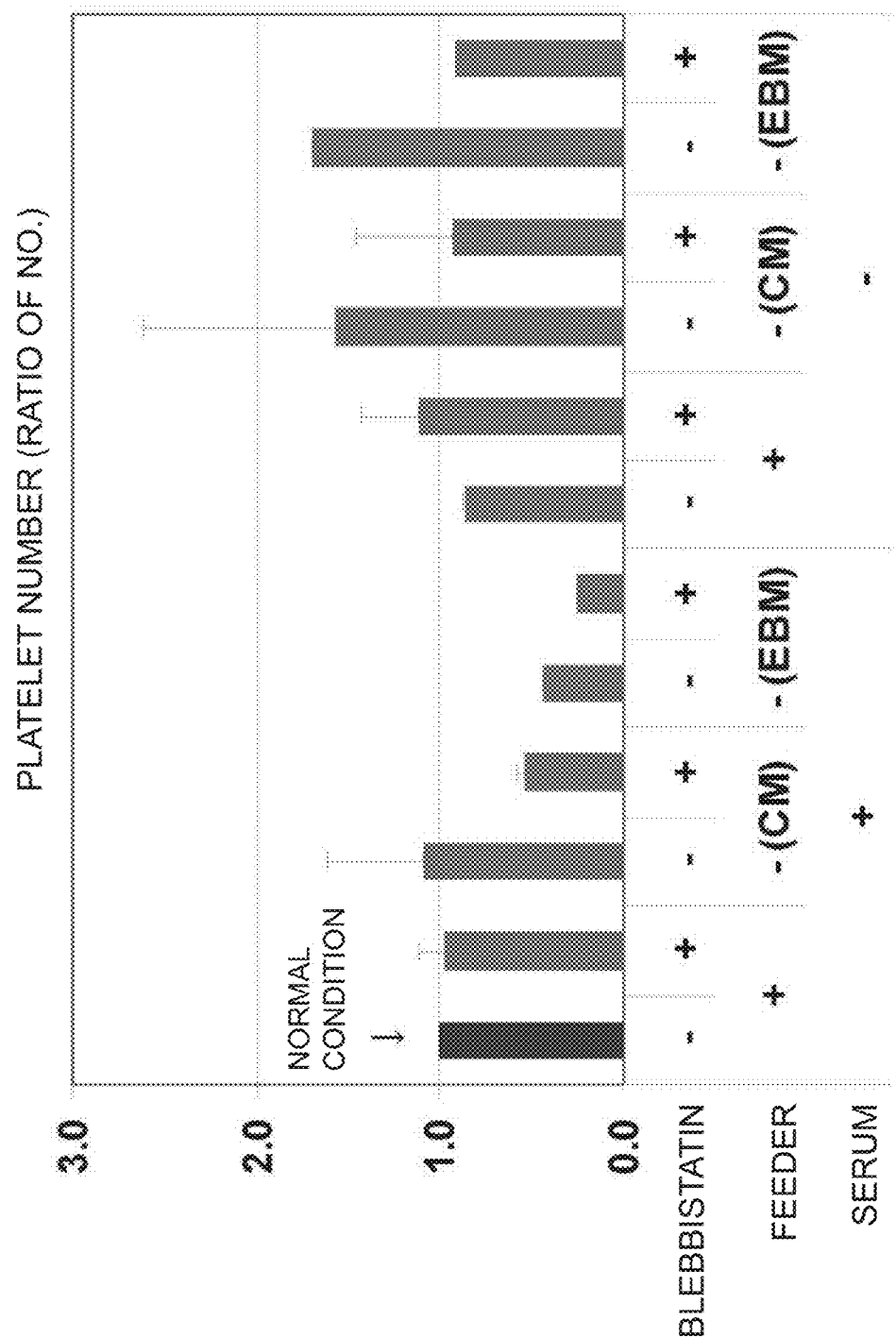

FIG. 17 It shows the results of studying the influence of the presence or absence of a serum, feeder cells, and blebbistatin on the number of platelets.

Figure 18:
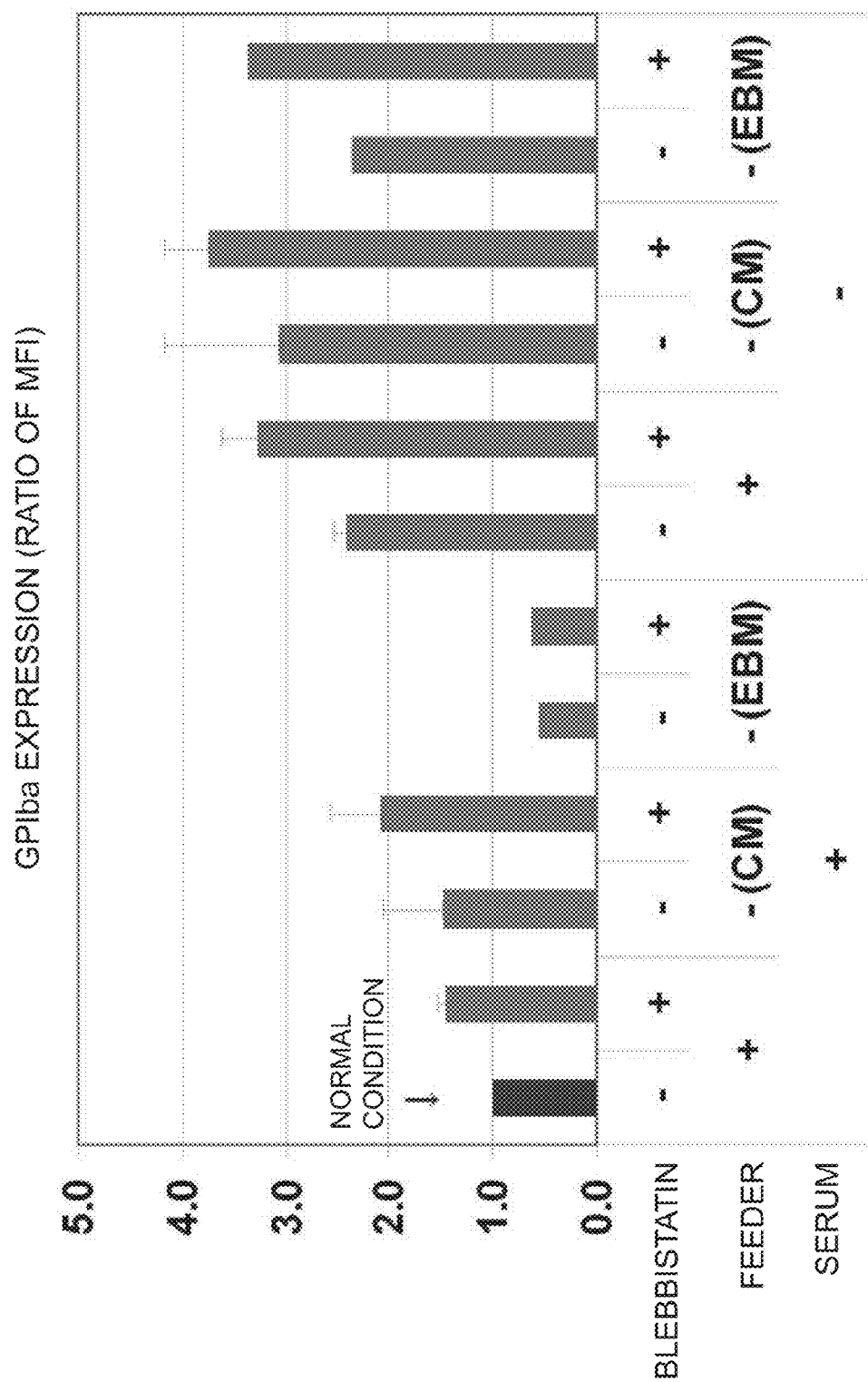

FIG. 18 It shows the results of studying the influence of a serum, feeder cells, and blebbistatin on the ratio of CD42b platelets.

Figure 19:
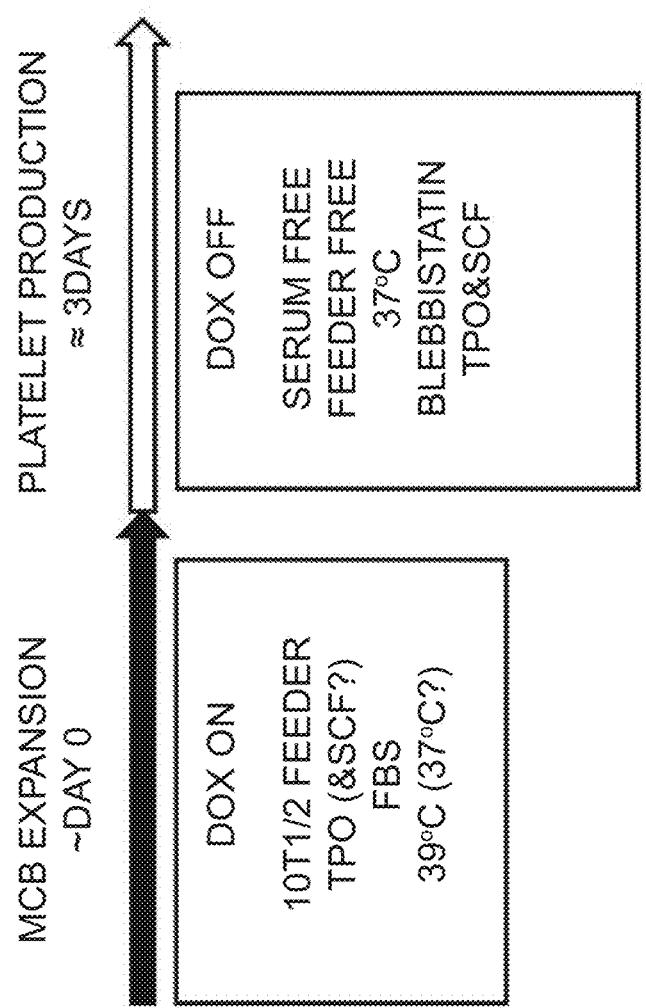

FIG. 19 It shows one example of preferable culturing conditions in the polyploidization step (MCB expansion) of megakaryocytes and during a platelet release stage (platelet production).

Figure 20:
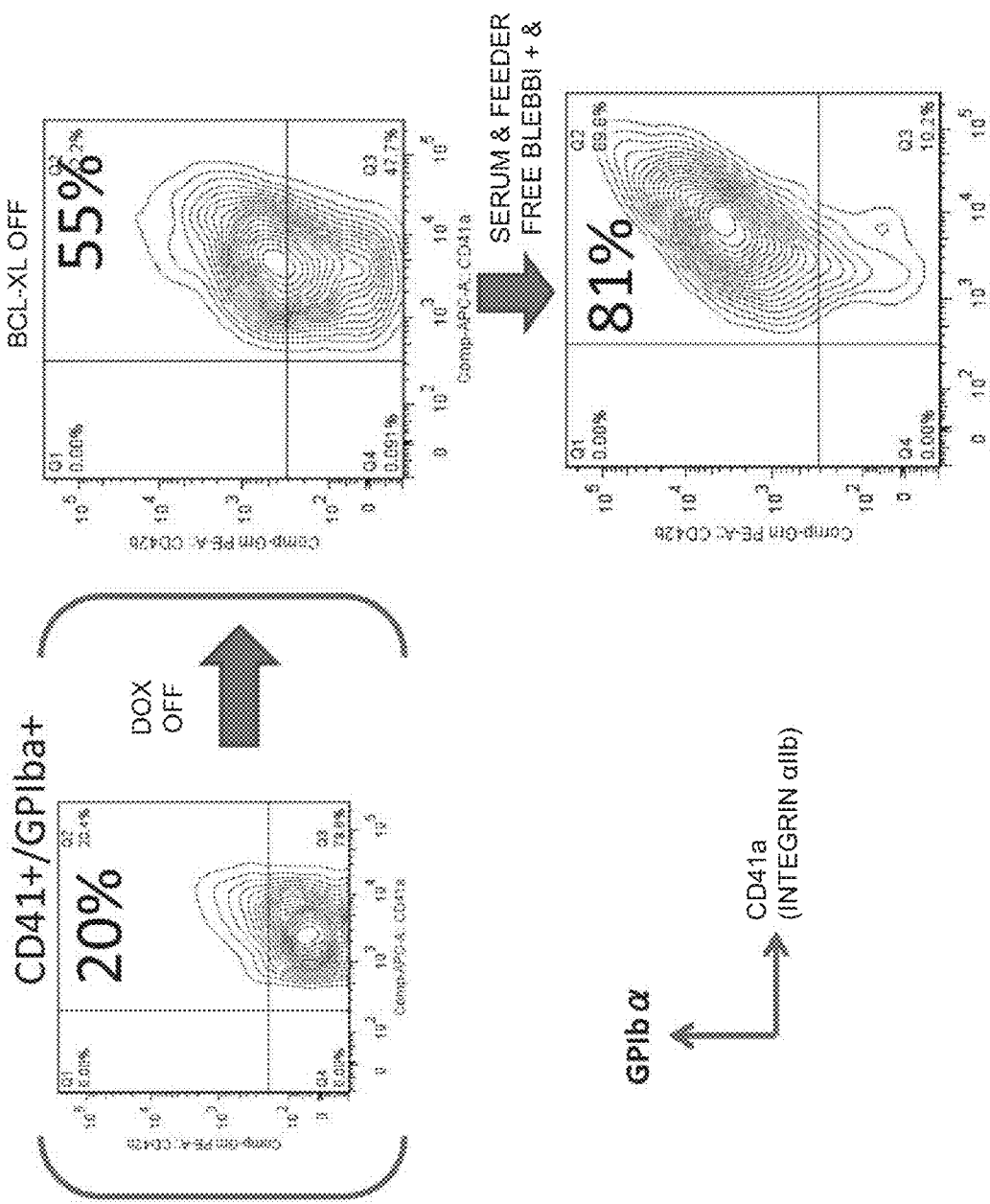

FIG. 20 It shows an increase in a ratio of CD42b platelets by the suppression of expression of BCL-XL and a further increase in a ratio of CD42b platelets by removing the serum and feeder cells from the medium and adding blebbistatin.

Figure 21:
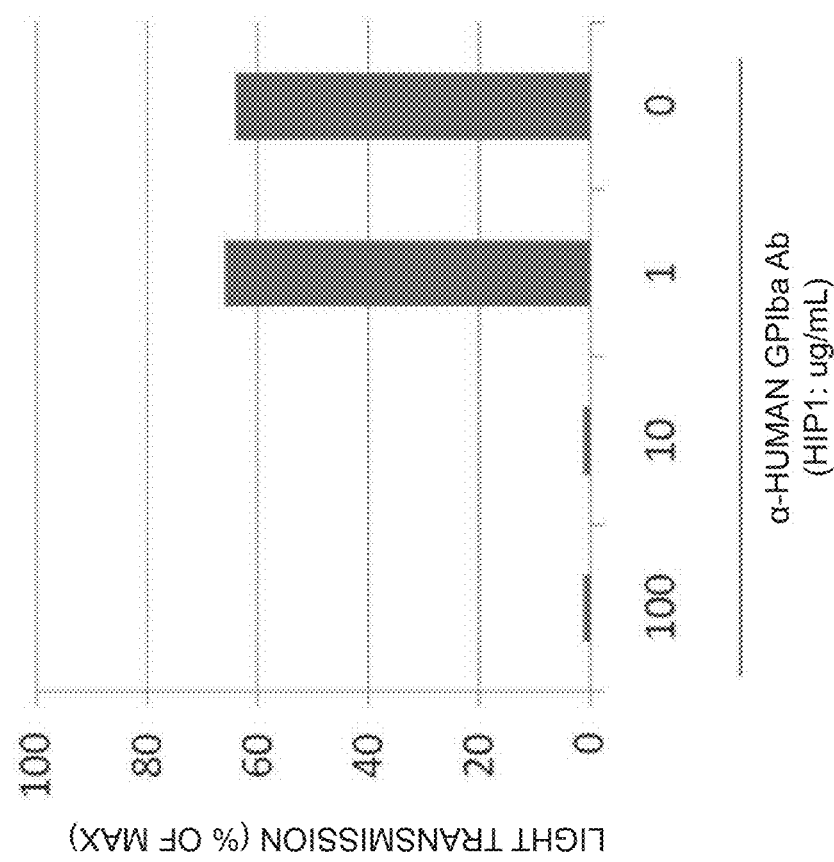

FIG. 21 It shows the results of studying the influence of a functional inhibitory antibody HIP1 against CD42b on the ristocetin agglutination effect of peripheral platelets.

Figure 22:
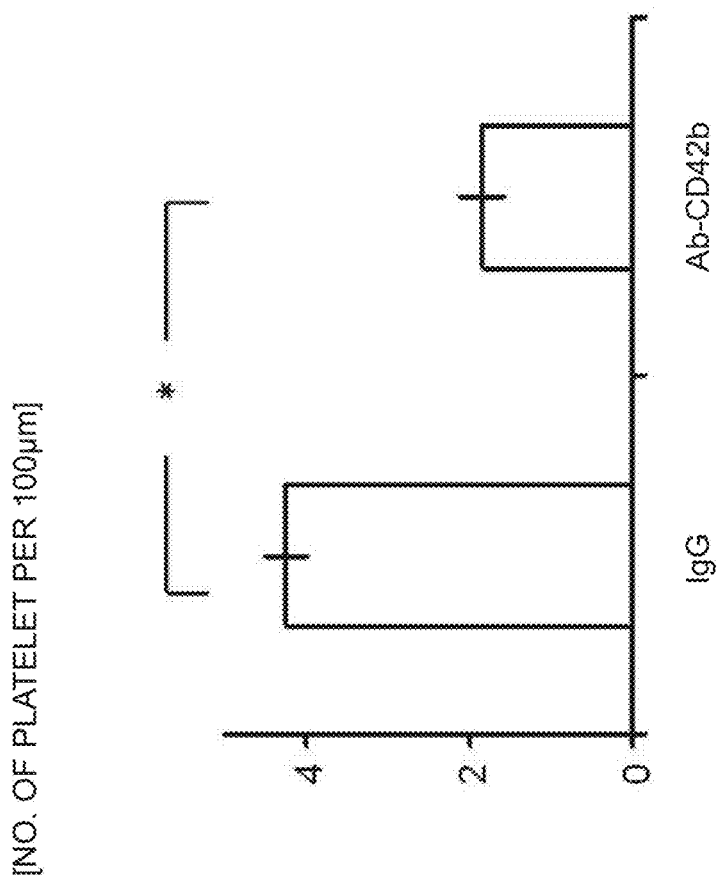

FIG. 22 It shows the results of studying the influence of a functional inhibitory antibody HIP1 against CD42b on thrombus formation in vivo.

Figure 23:
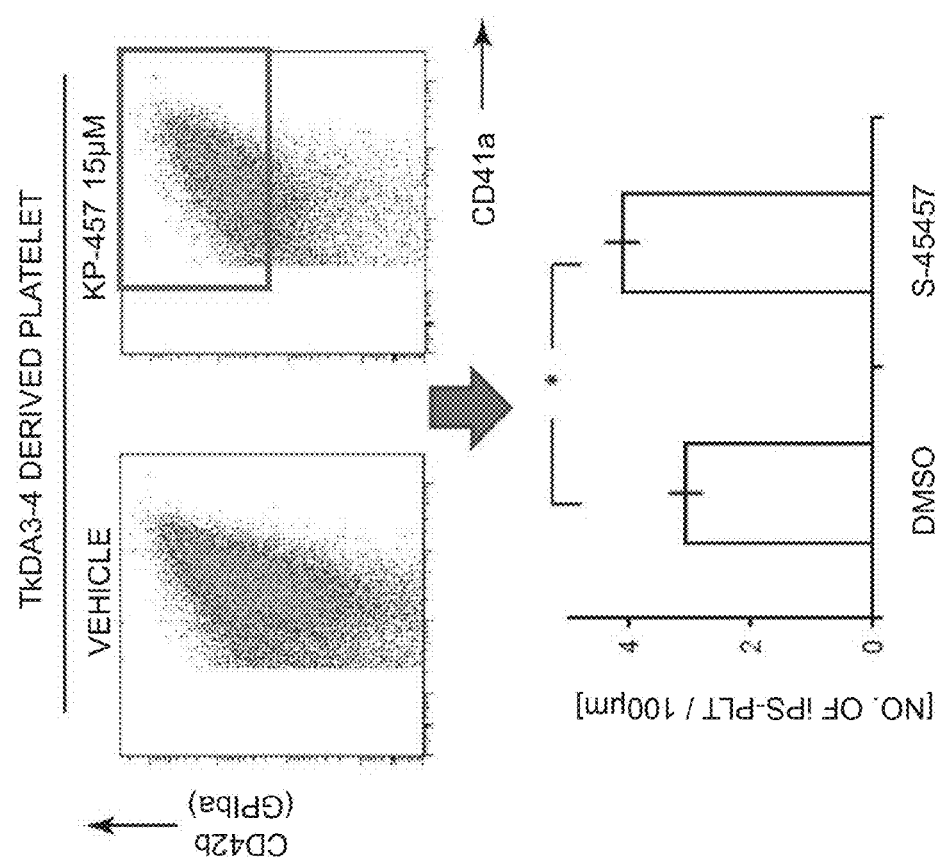

FIG. 23 It shows the results of respectively transplanting, to NOG mice, iPS cell-derived platelets produced while adding KP-457 (S-45457), an ADAM17 inhibitor and thereby increasing the expression level of GPIbα (CD42b) and iPS cell-derived platelets produced without adding an ADAM17 inhibitor and measuring the number of platelets which contributed to thrombus formation.

Figure 24:
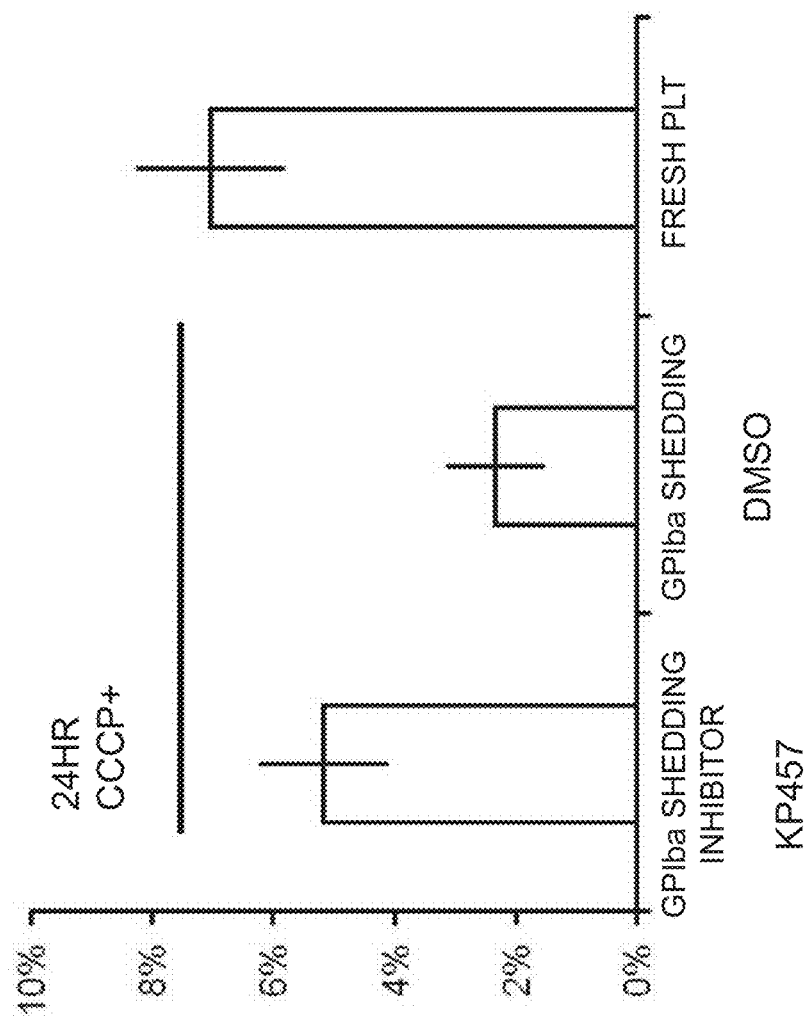

FIG. 24 It shows the results of transplanting human peripheral platelets spuriously deteriorated by adding 100 µm of CCCP, a platelet damaging agent in the presence of KP-457, platelets to which CCCP was added in the absence of KP-457, and fresh platelets, respectively and measuring the number of platelets which contributed to thrombus formation.

MODE FOR CARRYING OUT THE INVENTION (Method of Producing Polyploidized Megakaryocytes)

The present invention provides a method of promoting polyploidization of megakaryocytes and thereby preparing polyploidized megakaryocytes.

One mode of the method of producing polyploidized megakaryocytes according to the present invention includes a step of forcing expression of an apoptosis suppressor gene in megakaryocytes before polyploidization and culturing the cells.

The term "megakaryocytes before polyploidization" as used herein is not particularly limited and may refer to megakaryocytes which are available from the cord blood or bone marrow cells and whose polyploidization has not proceeded sufficiently, or megakaryocytes which have been inductively differentiated from ES cells, iPS cells, hematopoietic stem cells derived from cord blood, bone marrow blood, or peripheral blood, progenitor cells, or the like and whose polyploidization has not proceeded sufficiently.

Further, the term "megakaryocytes before polyploidization" as used herein embraces cells that are characterized, for example, as CD41a positive/CD42a positive/CD42b positive.

The term "polyploidized megakaryocytes" or "megakaryocytes which have undergone polyploidization" means cells or a cell population in which the number of nuclei has increased relatively compared with "megakaryocytes before polyploidization". For example, when megakaryocytes to which the method of the present invention is to be applied have a 2N nucleus, cells having a 4N or greater nucleus correspond to "polyploidized megakaryocytes" or "megakaryocytes which have undergone polyploidization". Even in megakaryocytes before polyploidization, the number of nuclei is not limited to one. In a cell population, the number of nuclei in the whole cell population shows a significant increase after a predetermined term, the cell population before the predetermined term may be called "megakaryocytes before polyploidization" and the cell population after a predetermined term may be called "megakaryocytes which have undergone polyploidization".

The present invention can also be applied to megakaryocytes before polyploidization which have been inductively differentiated from pluripotent stem cells (such as ES cells and iPS cells), hematopoietic stem cells derived from cord blood, bone marrow blood, or peripheral blood, and progenitor cells. For example, megakaryocytes available from a net-like structure (which may also be called ES-sac or iPS-sac) prepared from ES cells or iPS cells are preferred. Here, the "net-like structure" prepared from ES cells or iPS cells means a steric sac (having an internal space) like structure derived from ES cells or iPS cells. It is made of an endothelial cell population and the like and contains therein hematopoietic progenitor cells (refer to Patent Document 1, Patent Document 2, and Non-patent Document 2).

No particular limitation is imposed on ES cells to be used in the present invention and it is possible to use those established finally as an ES cell line by culturing fertilized eggs in the blastocyst stage together with feeder cells, isolating proliferating cells derived from the inner clump of cells into individual cells, and repeating subculture.

When iPS cells are used, cells of any origin can be used insofar as they have acquired pluripotent differentiation similar to ES cells by introducing several kinds of transcription factor (which will hereinafter be called "pluripotent differentiation factor") genes capable of providing somatic cells (for example, fibroblasts or blood cells) with pluripotent differentiation. As the pluripotent differentiation factors, many factors have already been reported. Examples include, but not limited to, Oct family (ex. Oct3/4), SOX family (ex. SOX2, SOX1, SOX3, SOX15, and SOX17), Klf family (ex. Klf4, and Klf2), MYC family (ex. c-MYC, N-MYC, and L-MYC), NANOG, and LIN28.

The present inventors have reported that by forcing expression of an oncogene such as MYC and a gene such as BMI1 in megakaryocytes before polyploidization (including those called "megakaryocytic progenitor cells" in Patent Document 3) derived from pluripotent stem cells, the resulting megakaryocytes have enhanced proliferative capacity (Patent Document 3, JEM, 207: 2817-2830 2010).

The megakaryocytes before polyploidization obtained using the above-mentioned method are suited for use in the method of the present invention.

In the method of producing polyploidized megakaryocytes according to the present invention, as the megakaryocytes before polyploidization, those obtained by a step of, in any differentiation stage from hematopoietic progenitor cells to megakaryocytes before proliferation, forcing expression of an oncogene and any of the following genes (i) to (iii):

(i) a gene suppressing the expression of a p16 gene or a p19 gene;
(ii) a gene suppressing the expression of an Ink4a/Arf gene; and
(iii) a polycomb gene;
and culturing and proliferating the resulting cells.

Examples of the oncogene include MYC family gene, Src family gene, Ras family gene, Raf family gene, and protein kinase family genes such as c-Kit, PDGFR, and Abl. Examples of the genes (i) to (iii) include BMI1, Mel18, Ring1a/b, Phc1/2/3, Cbx2/4/6/7/8, Ezh2, Eed, Suz12, HADC, and Dnmt1/3a/3b, with a BMI1 gene being particularly preferred. Control of the expression of the oncogene and the polycomb gene can be conducted by those skilled in the art in a conventional manner. For example, the method described in detail in Patent Document 3 and the like can be used. The oncogene and any one of the genes (i) to (iii) may be introduced into the cells at any stage of hematopoietic progenitor cells to megakaryocytes before polyploidization. However, this is not limited as expression of these genes is induced in the megakaryocytes before polyploidization to be used in the present invention.

The oncogene and the genes (i) to (iii) (for example, a BMI1 gene) to be used in the present invention include not only genes having an already known cDNA sequence but also homologs identified using prior art based on homology to the known cDNA sequence.

For example, among MYC family genes, the c-MYC gene is a gene having a nucleic acid sequence of SEQ ID NO: 1. Homologs of the c-MYC gene are genes having a cDNA sequence substantially the same as the nucleic acid sequence of SEQ ID NO: 1. The cDNA having a sequence substantially the same as the nucleic acid sequence of SEQ ID NO: 1 is a DNA having about 60% or greater sequence identity, preferably about 70% or greater sequence identity, more preferably about 80%, 81%, 82%, 83%, 84%, 85%, 86%, 87%, 88%, 89%, 90%, 91%, 92%, 93%, 94%, 95%, 96%, 97%, or 98% sequence identity, most preferably about 99% sequence identity to a DNA having a sequence of SEQ ID NO: 1, or a DNA capable of being hybridized with a DNA having a sequence complementary to the nucleic acid sequence of SEQ ID NO: 1 under stringent conditions, where a protein encoded by such a DNA contributes to amplification of cells at a differentiation stage such as megakaryocytes before polyploidization.

The BMI1 gene is a gene having a nucleic acid sequence of, for example, SEQ ID NO: 2. A homolog of the BMI1 gene is a gene having a cDNA sequence substantially the same as the nucleic acid sequence of, for example, SEQ ID NO: 2. The cDNA having a sequence substantially the same as the nucleic acid sequence of SEQ ID NO: 2 is a DNA having about 60% or greater sequence identity, preferably about 70% or greater sequence identity, more preferably about 80%, 81%, 82%, 83%, 84%, 85%, 86%, 87%, 88%, 89%, 90%, 91%, 92%, 93%, 94%, 95%, 96%, 97%, or 98% sequence identity, most preferably about 99% sequence identity to a DNA having a sequence of SEQ ID NO: 2, or a DNA capable of being hybridized with a DNA having a sequence complementary to the nucleic acid sequence of SEQ ID NO: 2 under stringent conditions, where a protein encoded by such a DNA suppresses oncogene-induced senescence in the cells in which the oncogene such as the MYC family gene has been expressed, thereby promoting amplification of the cells.

The above-mentioned oncogene and the genes (i) to (iii) are necessary for cell proliferation, but they may inhibit promotion of polyploidization or release of platelets so that expression of these genes may be suppressed prior to a polyploidization step. Suppression of the expression of these genes in the cells facilitates release of functional platelets (Patent Document 3).

The term "apoptosis suppressor gene" as used herein is not particularly limited insofar as it is a gene suppressing apoptosis. Examples of it include a BCL2 gene, a BCL-XL gene, Survivin, and MCL1.

The present inventors have found that when forced expression of the oncogene and any of the genes (i) to (iii) is suppressed, death of the proliferated megakaryocytes before polyploidization can be induced. As shown later in Examples, suppression of expression of the oncogene and any of the genes (i) to (iii) in the megakaryocytes before polyploidization and forced expression of an apoptosis suppressor gene in the cells promote the polyploidization of the megakaryocytes, resulting in efficient production of platelets from the megakaryocytes before polyploidization.

As shown later in Examples, megakaryocytes continue long-term proliferation by forcing expression of an apoptosis suppressor gene.

Apoptosis suppressor genes such as BCL-XL gene and BCL2 gene to be used in the present invention include not only genes whose cDNA sequence has already been published but also homologs identified by prior art based on homology to the known cDNA sequence. For example, a BCL-XL gene, one of apoptosis suppressor genes, is a gene having a nucleic acid sequence of SEQ ID NO: 3. A homolog of the BCL-XL gene is a gene having a cDNA sequence substantially equal to the nucleic acid sequence of SEQ ID NO: 3. The cDNA having a sequence substantially equal to the nucleic acid sequence of SEQ ID NO: 3 is a DNA having about 60% or greater sequence identity, preferably about 70% or greater sequence identity, more preferably about 80%, 81%, 82%, 83%, 84%, 85%, 86%, 87%, 88%, 89%, 90%, 91%, 92%, 93%, 94%, 95%, 96%, 97%, or 98% sequence identity, most preferably 99% sequence identity to a DNA having a sequence of SEQ ID NO: 3, or a DNA capable of being hybridized with a DNA having a sequence complementary to the nucleic acid sequence of SEQ ID NO: 3 under stringent conditions, where a protein coded by such DNA is effective for suppressing apoptosis.

The term "stringent conditions" as used herein means hybridization conditions easily determined by those skilled in the art, and are empirical experimental conditions that typically depend on a probe length, a washing temperature, and a salt concentration. Usually, a temperature for proper annealing becomes higher when a longer probe is used, and becomes lower when a shorter probe is used. Hybrid formation usually depends on reannealing ability of a complementary strand placed in an environment where a temperature is slightly lower than its melting point.

Under low stringent conditions, for example, in a filter washing stage after hybridization, a filter is washed in a 0.1×SSC, 0.1% SDS solution under temperature conditions of from 37° C. to 42° C. Under high stringent conditions, for example, in the washing stage, a filter is washed in a 5×SSC, 0.1% SDS solution at 65° C. Polynucleotide with higher homology can be obtained by making the stringent conditions higher.

In order to force expression of genes such as oncogene, genes (i) to (iii), and apoptosis suppressor gene in cells, any method well known to those skilled in the art may be employed. For example, the gene may be introduced into cells by using a gene introduction system with a lentivirus or a retrovirus, and then expressed. When gene expression is conducted using a viral gene introduction vector, a target gene may be expressed by operably linking the gene to the downstream of an appropriate promoter, inserting the resulting gene into the gene introduction vector, and then introducing it into the cells. Here, the term "operably linking" means that a target gene is linked in to a promoter to achieve desired expression of the target gene. In embodiments of the present invention, for example, the target gene may be constantly expressed using a CMV promoter, an EF1 promoter, or the like. Alternatively, an appropriate promoter (inducible promoter) may be placed under control of an element having activity controlled by a trans factor, e.g., a drug response element such as tetracycline response element and a target gene may be inductively expressed by conducting such a control as drug addition. Since such a gene expression system using a drug can realize desired expression control of the oncogene or the genes (i) to (iii), an appropriate system can be easily selected by those skilled in the art. A commercially available kit may be used in order to conduct such expression. The oncogene and the genes (i) to (iii), which are the target genes in expression control, may be inserted into respective vectors or in one vector.

Suppression of expression of the oncogene or any of the genes (i) to (iii) in megakaryocytes may be achieved, for example, by removing the drug or the like and thereby releasing the induction of expression using the above-mentioned inductive expression system. Alternatively, the oncogene or any of the genes (i) to (iii) which has been introduced may be removed using a Cre/lox system or the like to suppressively control the expression of these genes. A commercially available kit or the like may be used as needed in order to suppressively regulate the expression of the oncogene or the gene (i) to (iii).

One mode of the method of producing polyploidized megakaryocytes according to the present invention includes a step of forcing expression of an apoptosis suppressor gene in cells, and in parallel, inhibiting expression or function of a p53 gene product in the cells. The term "expression" is used as a concept encompassing transcription and translation. For example, the term "inhibiting expression" may include the meaning "inhibiting in a transcription level" or "inhibiting in a translation level".

The p53 gene product is widely known as a tumor suppressor gene and its sequence and the like in various animal species are known.

A method of inhibiting the function of the p53 gene product in megakaryocytes can be achieved by a conventional technology in this technical field. Examples of the method include a method of introducing mutation (substitution, insertion, or deletion, or alteration or modification) into a P53 gene and thereby inhibiting production of the gene product and a method of directly inhibiting the function of the gene product. Examples of the method of directly introducing mutation (substitution, insertion, or deletion, or alteration or modification) into a gene include a method of destructing the whole p53 gene through homologous recombination while making use of an appropriate gene targeting vector and a method of introducing mutation in a region important for activity of the gene product by making use of a Cre/lox system or the like.

As a method of inhibiting the function of the p53 gene product, a dominant negative method may be used. The dominant negative method is a method of inducing in cells abundant expression of a p53 protein having mutation introduced therein to reduce or deprive its activity, making a ratio of the p53 protein inert to the normal p53 protein in cells overwhelmingly high, and thereby obtaining cells showing a behavior of cells which have lost the function of the p53 protein.

As the method suppressing the expression of the p53 gene product, an antisense method, a ribozyme method, an RNAi method, or the like may be used.

The antisense method is a method of suppressing expression of a gene by using a single stranded nucleic acid having a base sequence complementary to a target gene (basically, an mRNA as a transcription product) and having usually a length of from 10 bases to 100 bases, preferably from 15 bases to 30 bases. The gene expression is inhibited by introducing an antisense nucleic acid in cells and hybridizing it with the target gene. The antisense nucleic acid is not completely complementary to the target gene insofar as an expression inhibiting effect of the target gene can be produced. The antisense nucleic acid can be designed as needed by those skilled in the art by using known software or the like. The antisense nucleic acid may be any of DNA, RNA, and DNA-RNA chimera, or may be modified.

A ribozyme is a nucleic acid molecule catalytically hydrolyzes a target RNA and is composed of an antisense region having a sequence complementary to the target RNA and a catalyst center region involved in cleavage reaction. A ribozyme can be designed as needed in a known manner by those skilled in the art. A ribozyme is usually an RNA molecule, but a DNA-RNA chimera molecule may be used instead.

The RNAi method is a sequence-specific gene expression suppressing mechanism induced by a double stranded nucleic acid. The method has high target specificity and in addition, is highly safe because it utilizes a gene expression suppressing mechanism originally present in vivo.

Examples of the double stranded nucleic acid having an RNAi effect include siRNA. When siRNA is used for mammalian cells, it is a double stranded RNA having usually from about 19 to 30 bases, preferably from about 21 to 25 bases. The double stranded nucleic acid having an RNAi effect usually has, as one of the strands, a sequence complementary to a portion of a target nucleic acid and, as the other strand, a sequence complementary thereto.

The double stranded nucleic acid having an RNAi effect can be designed in a known manner based on the base sequence of a target gene. The double stranded nucleic acid having an RNAi effect may be any of a double stranded RNA, a DNA-RNA chimera type double stranded nucleic acid, an artificial nucleic acid, and a nucleic acid subjected to various modifications.

The siRNA, antisense nucleic acid, and ribozyme can be expressed in cells by introducing, into the cells, vectors (for example, lentivirus vectors) containing the nucleic acids encoding them, respectively. As the siRNA, DNAs encoding two strands, respectively, may be used or a DNA encoding a single stranded nucleic acid obtained by linking the two strands of a double stranded nucleic acid via a loop may be used. In the latter case, the single stranded RNA obtained by intracellular transcription has a hairpin type structure because the complementary portion of it is hybridized in the molecules. This RNA is called shRNA (short hairpin RNA). When the ShRNA is exported to the cytoplasm, the loop portion is cleaved by an enzyme (Dicer) to be a double stranded RNA and it produces an RNAi effect.

As another method of inhibiting the function of the p53 gene product in megakaryocytes, a method of directly or indirectly inhibiting the function of the p53 gene product, a method of inhibiting phosphorylation of p53 and thereby indirectly inhibiting the activation of p53, or the like method can be employed.

As described later in Examples, megakaryocytes before forced expression of an apoptosis suppressor gene and inhibition of expression or function of the p53 gene product, continue proliferation, wherein the megakaryocytes whose cytokine dependence is SCF and platelets released therefrom are not CD42b positive are included. When forced expression of an apoptosis suppressor gene and inhibition of expression or function of the p53 gene product are conducted, megakaryocytes are partially polyploidized while continuing proliferation and release many CD42-positive platelets. At this stage, the cytokine dependence of megakaryocytes changes from SCF to TOP and proliferation and maturation proceed in parallel to each other.

One mode of the method of producing polyploidized megakaryocytes according to the present invention includes at least one of a step of treating the cells in which an apoptosis suppressor gene has been forcibly expressed while culturing them, with (a) an actomyosin complex function inhibitor, (b) an ROCK inhibitor, and (c) an HDAC inhibitor. By the above-mentioned treatment, more stable proliferation and polyploidization proceed.

The term "actomyosin complex" as used herein means a complex between actin and myosin II and it constitutes, for example, a contractile ring which will appear at the time of cytokinesis. In the actomyosin complex, myosin II functions as a motor protein while interacting with actin and is involved in contraction of the contractile ring and the like. The "actomyosin complex function inhibitor" in the present invention may inhibit the function by any mechanism. It includes, for example, those inhibiting the formation of an actomyosin complex and thereby inhibiting the function of the actomyosin complex; those inhibiting myosin heavy chain (MHC) IIA/IIB ATPase and thereby inhibiting the function of the actomyosin complex; and those inhibiting myosin light chain kinase (MlCK) and thereby inhibiting the function of the actomyosin complex. The myosin heavy chain IIA/B ATPase is a molecule having an important role in contraction of a contractile ring, while the myosin light chain kinase phosphorylates L2, among myosin light chains, and induces a sliding movement between actin and myosin.

It has been reported to date that an ROCK inhibitor suppresses endomitosis of megakaryocytes and promotes polyploidization. The myosin heavy chain IIA/B ATPase or myosin light chain kinase that controls formation or function of an actomyosin complex functions downstream of an ROCK signal and more directly controls contraction of a contractile ring via formation or function regulation of an actomyosin complex. The actomyosin complex function inhibitor is therefore presumed to suppress endomitosis of megakaryocytes more effectively and promote polyploidization more, compared with the ROCK inhibitor.

Examples of the actomyosin complex function inhibitor usable in the present invention include blebbistatin (Science, 299: 1743-1747 2003), a myosin heavy chain IIA/B ATPase inhibitor and ML7, a myosin light chain kinase inhibitor. As the myosin heavy chain IIA/B ATPase inhibitor or myosin light chain kinase inhibitor, nucleic acids (for example, shRNA) or antibodies inhibiting the activity of myosin heavy chain IIA/B ATPase or myosin light chain kinase can also be used.

It is to be noted that the term "treatment" as used herein means an operation conducted to produce the effect of an inhibitor or the like in target cells, for example, addition of an adequate amount of an inhibitor or the like to a culture medium of cells to incorporate it in the cells. In some cases, an operation that promotes incorporation of it in cells may be used in combination.

One mode of the method of producing megakaryocytes according to the present invention includes a step of treating the cells in which an apoptosis suppressor gene has been forcibly expressed with an ROCK inhibitor while culturing them.

Examples of the ROCK (Rho-associated coiled-coil forming kinase/Rho associated kinase) inhibitor include [(R)-(+)-trans-N-(4-pyridyl)-4-(1-aminoethyl)-cyclohexane carboxamide.2HCl.H$_2$O] (Y27632). In some cases, antibodies or nucleic acids (for example, shRNA) that inhibit Rho kinase activity can also be used as the ROCK inhibitor.

One mode of the method of producing megakaryocytes according to the present invention includes a step of treating the cells in which an apoptosis suppressor gene has been forcibly expressed with an HDAC inhibitor while culturing the cells.

The HDAC inhibitor has an action of inhibiting histone deacetylase (HDAC) activity. Many HDAC inhibitors have been known to date. Examples of it include valproic acid, trichostatin A, SAHA (suberoylanilide hydroxamic acid), and APHA (aroyl-pyrrolyl-hydroxyamide). In particular, valproic acid and trichostatin A are preferably used. When a drug to be used is provided in the form of salt, the inhibitor may be used in the form of salt.

The optimum concentration when the cells are treated with an actomyosin complex function inhibitor, ROCK inhibitor, HDAC inhibitor, or the like can be determined in advance by those skilled in the art based on the results of a preliminary test. The treatment time, method or the like can also be selected as needed by those skilled in the art. For example, when the cells are treated with blebbistatin, a myosin heavy chain II ATPase inhibitor, it may be added in an amount of from about 2 to 15 µg/ml or from about 5 to 10 µg/ml to a culture medium and cultured, for example, preferably for from about 5 to 10 days, particularly preferably for from about 6 to 7 days. Y27632, a ROCK inhibitor may be added in an amount of from 5 to 15 µM or from 8 to 12 µM, preferably from about 10 µM, while valproic acid, an HDAC inhibitor may be added in an amount of from about 0.1 to 1 mM or from about 0.2 to 0.7 mM, preferably about 0.5 mM. Treatment time with Y27632 or valproic acid may be for from 10 to 21 days, preferably for about 14 days.

One mode of the method of producing polyploidized megakaryocytes according to the present invention includes placing megakaryotic cells at a temperature of 37° C. or greater, in which an apoptosis suppressor gene in the cells has been forcibly expressed while culturing the cells.

It has been confirmed that culturing megakaryocytes at a usual temperatures of 37° C. or greater promotes differentiation of megakaryocytes which have undergone polyploidization. The "temperatures of 37° C. or greater" is, for example, from about 37° C. to about 42° C., preferably from about 37° C. to about 39° C., because temperatures not giving damage to cells are adequate. Although a culturing term at temperatures of 37° or greater can be determined as needed while monitoring the number of megakaryocytes which have undergone polyploidization, it is, for example, from 10 days to 28 days, preferably from 14 days to about 21 days.

No particular limitation is imposed on the other culturing conditions in the step of conducting forced expression of an apoptosis suppressor gene in megakaryocytes which have not undergone polyploidization and then culturing the resulting cells insofar as the effect of the present invention can be produced preferably under the conditions. Known culturing conditions or conditions equivalent thereto can be used. For example, TPO, IL-1, IL-3, IL-4, IL5, IL-6, IL-9, IL-11, EPO, GM-CSF, SCF, G-CSF, Flt3 ligand, and Heparin may be used either singly or in combination of two or more and added to a medium.

Alternatively, a feeder cell may be used as needed for culturing.

The megakaryocytes which have undergone polyploidization obtained using the above-mentioned method efficiently produces CD42b-positive functional platelets. As shown later in Examples, the CD42b-positive platelets have high thrombus forming ability both in vivo and in vitro. In addition, the megakaryocytes which have undergone polyploidization can produce functional platelets even when thawed after cryopreservation.

The present invention also provides a blood cell composition having a high content of polyploidized megakaryocytes. The term "blood cell composition" may comprise, as well as "polyploidized megakaryocytes" whose polyploidization has been promoted by the method of the present invention, megakaryocytes prepared using another method, and the other blood cells.

Figure 11:
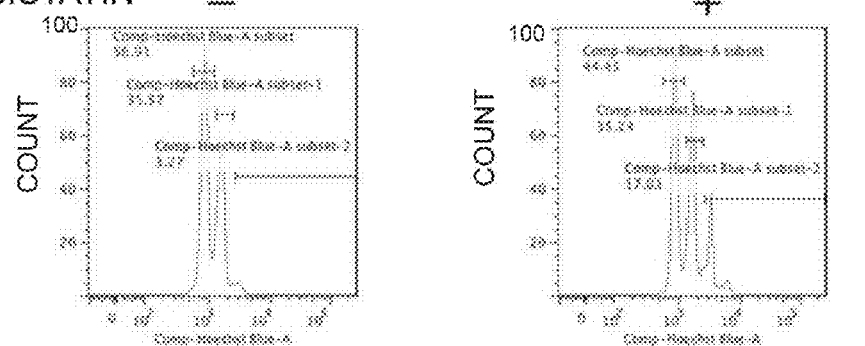
FIG. 11 Influence of a myosin heavy chain IIA/B ATPase inhibitor (actomyosin complex function inhibitor) on polyploidization of megakaryocytes. The degree of polymerization was studied after suppressing the expression of MYC/
Figure 11:
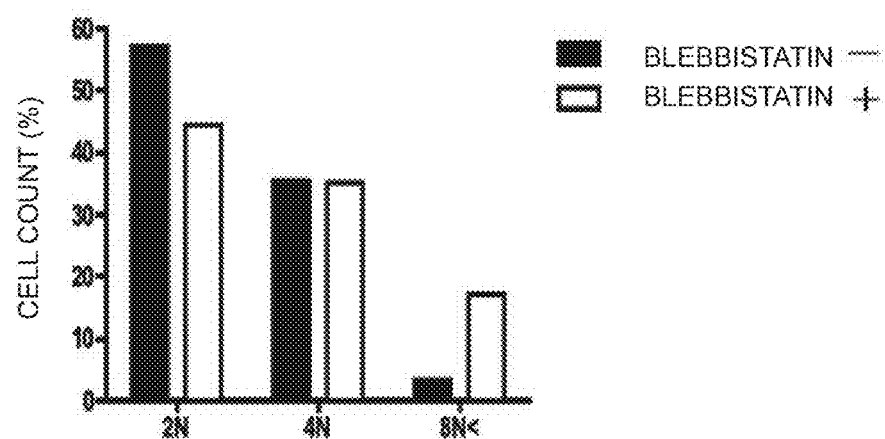

Treatment of the megakaryocytes before polyploidization by the method of the present invention can promote differentiation of them into polyploidized megakaryocytes of 4N or greater. Therefore, application of the method of the invention to a population of megakaryocytes differentiated, for example, from pluripotent stem cells or the like makes it possible to obtain a blood cell composition having a high content of polyploidized megakaryocytes of 4N or greater. When the population of megakaryocytes is treated using the method of the present invention, it is possible to increase the content of polyploidized megakaryocytes with 4N or greater to at least 20% or greater, 30% or greater, preferably 40% or greater, 50% or greater, more preferably 80% or greater (refer to, for example, FIG. 11B). Accordingly, the present invention makes it possible to prepare a population of megakaryocytes or a population of blood cells having a high existence ratio of polyploidized megakaryocytes.

Such a blood cell composition can also be cryopreserved. Therefore, such a blood cell composition is distributed in a frozen state and the method of producing platelets which will be described later may be conducted on the user side.

Megakaryocytes and the like which have been treated to promote polyploidization by the method of the present invention are effective also for transplanting them in vivo and producing functional platelets in vivo by a proper method.

At present, hematopoietic stem cells have been transplanted through bone marrow transplantation, cord blood transplantation, or the like. In particular, cord blood transplantation enables reduction of the problems of bone marrow transplantation such as shortage of number of donors and a great burden for donors so that there has recently been more opportunities of cord blood transplantation. The megakaryocytes produced in vivo by cord blood transplantation have however not undergone polyploidization sufficiently and it takes time to produce a sufficient number of platelets in vivo. When a production capacity of platelets should be increased rapidly, cord blood transplantation cannot satisfy this demand sufficiently at present.

Transplantation of polyploidized megakaryocytes obtained by using the method of the present invention can overcome the problems of bone marrow transplantation such as shortage of the number of donors and a heavy burden of donors and the problems of cord blood transplantation such as platelet production capacity in vivo. The method of the present invention is therefore much superior to the conventional transplantation methods.

(Production Method of Platelets)

The method of producing platelets according to the present invention, on the other hand, produces platelets in vitro from the polyploidized megakaryocytes and the like obtained using the method of the present invention.

The method of producing platelets according to the present invention includes a step of culturing the polyploidized megakaryocytes obtained by the above-mentioned method and collecting platelets from the cultured product.

Although no limitation is imposed on the culturing conditions, the polyploidized megakaryocytes may be cultured for from about 7 to 15 days, for example, in the presence of TPO (from about 10 to 200 ng/mL, preferably from about 50 to 100 ng/mL) or in the presence of TPO (from about 10 to 200 ng/mL, preferably from about 50 to 100 ng/mL), SCF (from 10 to 200 ng/mL, preferably about 50 ng/mL), and Heparin (from about 10 to 100 U/mL, preferably about 25 U/ml).

In one mode of the method of producing platelets according to the present invention, in the culturing step of polyploidized megakaryocytes, the above-mentioned forced expression of an apoptosis gene is suppressed or the above-mentioned apoptosis suppressor gene is removed from the polyploidized megakaryocytes.

The suppression of expression of an apoptosis suppressor gene may also be achieved, for example, by removing the chemical or the like to release the induction of expression by the above-mentioned inductive expression system. Alternatively, the apoptosis suppressor gene introduced may be removed by using a Cre/lox system and thereby expression of this gene may be suppressively controlled. A commercially available kit or the like can also be used as needed in order to suppressively regulate the expression of an apoptosis suppressor gene.

As shown later in Examples, when the expression of an apoptosis suppressor gene which has been forcibly expressed to promote polyploidization leads to an increase in production efficiency of CD41a-positive/CD42b-positive functional platelets.

Suppression of expression of or removal of an apoptosis suppressor gene is started 15 days, preferably 10 days, more preferably from 3 to 7 days, still more preferably about 3 days before collection of platelets.

In this step, expression of not only an exogenous apoptosis suppressor gene but also an endogenous apoptosis suppressor gene may be suppressed. Inhibition of the expression or function of a p53 gene product may be conducted successively after the present step.

The culturing temperature is not particularly limited insofar as the effect of the present invention can be produced. Culturing may be conducted at from 35° C. to 40° C., with from 37° C. to 39° being suited as shown later in Examples.

In the production method according to the present invention, the step of culturing polyploidized megakaryocytes may be conducted under serum-free and/or feeder cell-free conditions. As shown later in Examples, no large difference was found in the production amount of platelets between culturing in a medium containing a fetal bovine serum and culturing in a serum-free medium. However, a ratio of CD42b-positive platelets was greater when the cells was cultured in a serum-free medium or a feeder cell-free medium. If the platelet production step can be conducted in a serum-free and feeder cell-free medium, the platelets thus obtained can be used clinically without causing the problem of immunogenicity.

Production of platelets without using a feeder cell can suppress a production cost and is suited for mass production because adhesion of the feeder cell is not required and therefore suspension culture can be conducted in a flask or the like. When the feeder cell is not used, a conditioned medium may be used. The conditioned medium is not particularly limited and can be prepared by those skilled in the art in a known manner. For example, it can be obtained, for example, by culturing a feeder cell as needed and then removing the feeder cell from the cultured product by using a filter or the like.

In one mode of the method of producing platelets according to the present invention, a ROCK inhibitor and/or actomyosin complex function inhibitor is added to a medium. The ROCK inhibitor and actomyosin complex function inhibitor similar to those used in the above-mentioned method of producing polyploidized megakaryocytes can be used. Examples of the ROCK inhibitor include Y27632. Examples of the actomyosin complex function inhibitor include blebbistatin, a myosin heavy chain II ATPase inhibitor. The ROCK inhibitor may be added singly, the ROCK inhibitor and the actomyosin complex function inhibitor may be added individually; or they may be added in combination.

The ROCK inhibitor and/or actomyosin complex function inhibitor is added preferably in an amount of from 0.1 μM to 30 μM, for example, from 0.5 μM to 25 μM, from 5 μM to 20 μM, or the like.

The culturing term after addition of the ROCK inhibitor and/or actomyosin complex function inhibitor may be for one day to 15 days. It may be for 3 days, 5 days, 7 days, or the like. By adding the ROCK inhibitor and/or actomyosin complex function inhibitor, a ratio of CD42b-positive platelets can be increased further.

The embodiment of the present invention includes a kit for promoting polyploidization of megakaryocytes and producing mature megakaryocytes and/or platelets. The kit includes, as well as an expression vector and the like necessary for inducing intracellular expression of the oncogene, any of the above-mentioned genes (i) to (iii), a BCL-XL gene, or the like, and a reagent, a medium for culturing cells, a serum, a supplement such as growth factor (for example, TPO, EPO, SCF, Heparin, IL-6, IL-11, or the like), an antibiotic, and the like. In addition, the kit includes, when, for example, cells derived from ES cells or iPS cells are used, an antibody (for example, antibody against Flk1, CD31, CD34, UEA-I lectin, or the like) to confirm a marker for identifying a net-like structure prepared from these cells. The reagent, antibody, and the like included in the kit are supplied in any kind of vessels that enable a constituting ingredient to effectively keep its activity and cause neither adsorption of it to the material of the vessel nor deterioration of it.

The kit of the present invention may further include megakaryocytes before polyploidization in which the oncogene and any of the above-mentioned genes (i) to (iii) have been forcibly expressed.

The "cells" described herein are derived from humans and non-human animals (for example, mice, rats, cattle, horses, pigs, sheep, monkeys, dogs, cats, and birds). Although no particular limitation is imposed, human-derived cells are particularly preferred.

The present invention will hereinafter be described in further detail by showing Examples. It should however be borne in mind that the present invention is not limited to or by Examples.

EXAMPLES

1. Preparation of Megakaryocytes Before Polyploidization 1-1. Preparation of Megakaryocytes Before Polyploidization from ES Cells In order to study polyploidization of megakaryocytes, megakaryocytes before polyploidization were prepared from ES cells (refer to Patent Document 3 for details).

A human ES cell line [KhES-3] was cultured for 14 days in the presence of 20 ng/ml of VEGF to prepare a net-like structure. Hematopoietic progenitor cells removed from the resulting net-like structure were recovered and seeded on 10T1/2 cells to give a cell count of $1 \times 10^5$/well.

The hematopoietic progenitor cells thus prepared were infected with a c-MYC-2A-BMI1-containing pMx tet off c-MYC 2A BMI1 retrovirus vector three times every 12 hours at MOI=10 (confirmed using Jurkat cells) to induce expression of c-MYC and BMI1 (Patent Document 3). The pMx tet off c-MYC 2A BMI1 vector allows the expression of a c-MYC gene and a BMI1 gene in the presence of estradiol, while it suppresses the expression of the c-MYC gene and the BMI1 gene in the presence of doxycycline (Dox) and absence of estradiol.

Simultaneously with the first infection, 2 mM of estradiol was added and 12 hours after the final infection, the virus was removed. In that stage, the released amount of CD42b-positive platelets was small even if the expression of the c-MYC gene or BMI1 gene was turned off, suggesting that the cells were immature megakaryocytes. These immature cells may hereinafter be called "iMKPC-type I".

Figure 1A:
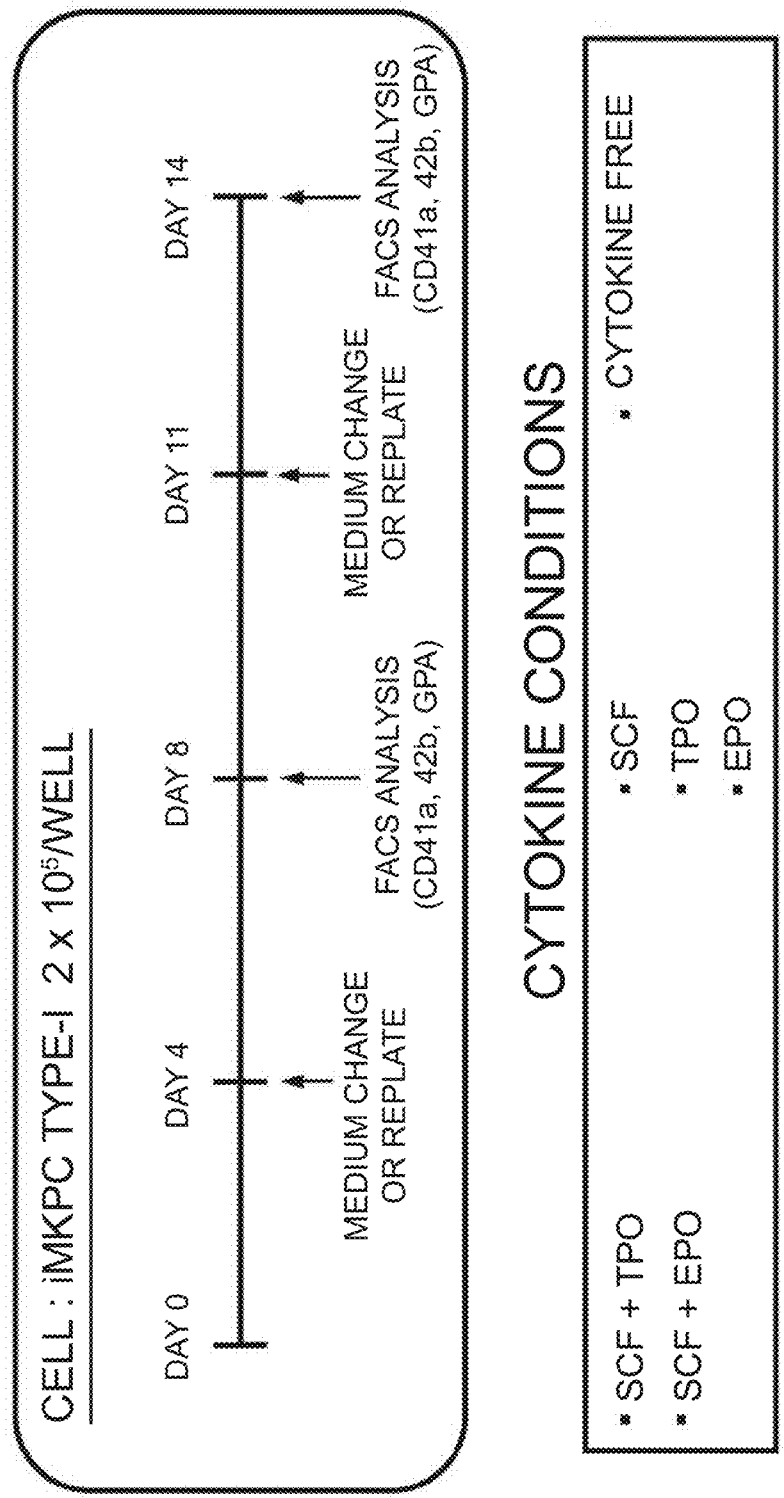
FIG. 1A It shows the outline of a test conducted to study cytokine dependence of iMKPC-type I proliferation.

The cytokine dependence of iMKPC-type I was studied by seeding $2\times10^5$ iMKPC-type I cells on 10T1/2 feeder cells and culturing them for 14 days at 37° C. under the conditions shown in FIG. 1A in the presence of 2 uM of β-estradiol while using the following cytokines: SCF (50 ng/ml), TPO (50 ng/ml), and EPO (6 U/ml). A population in which proliferation was confirmed on Day 4 and Day 11 was counted for cell number, and $2\times10^5$ cells were replated, while the medium of the other populations was changed. The number of cells was counted on Day 8 and Day 14 and $2\times10^5$ cells were replated. At the same time, on Day 8, some of the cells were analyzed with a flow cytometer after staining with a CD41 antibody, a CD42b antibody, and a GPA antibody.

Figure 1B:
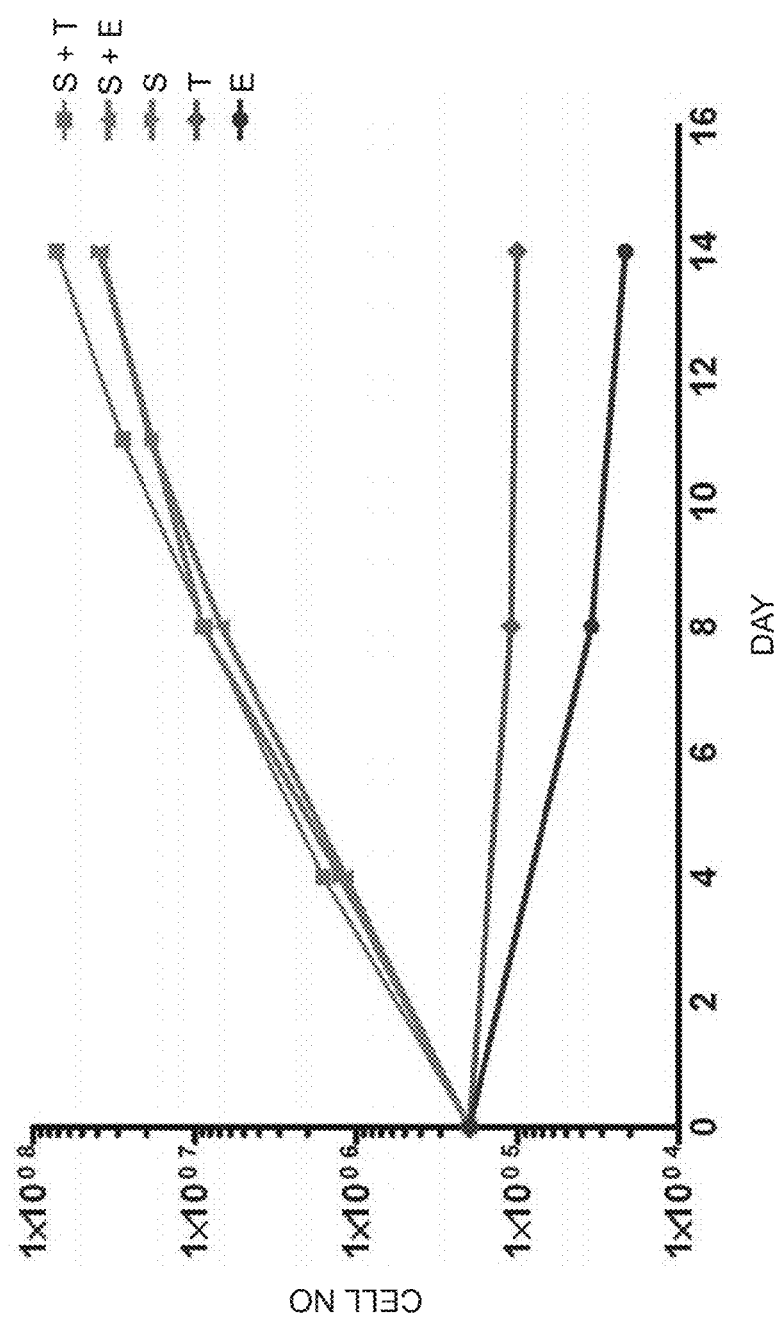
FIG. 1B It shows a change in the number of cells when iMKPC-type I was cultured in media to which SCF and TPO (S+T), SCF and EPO (S+E), SCF (S), TPO (T), and EPO (E) had been added, respectively, according to the schedule shown in FIG. 1A.
Figure 1C:
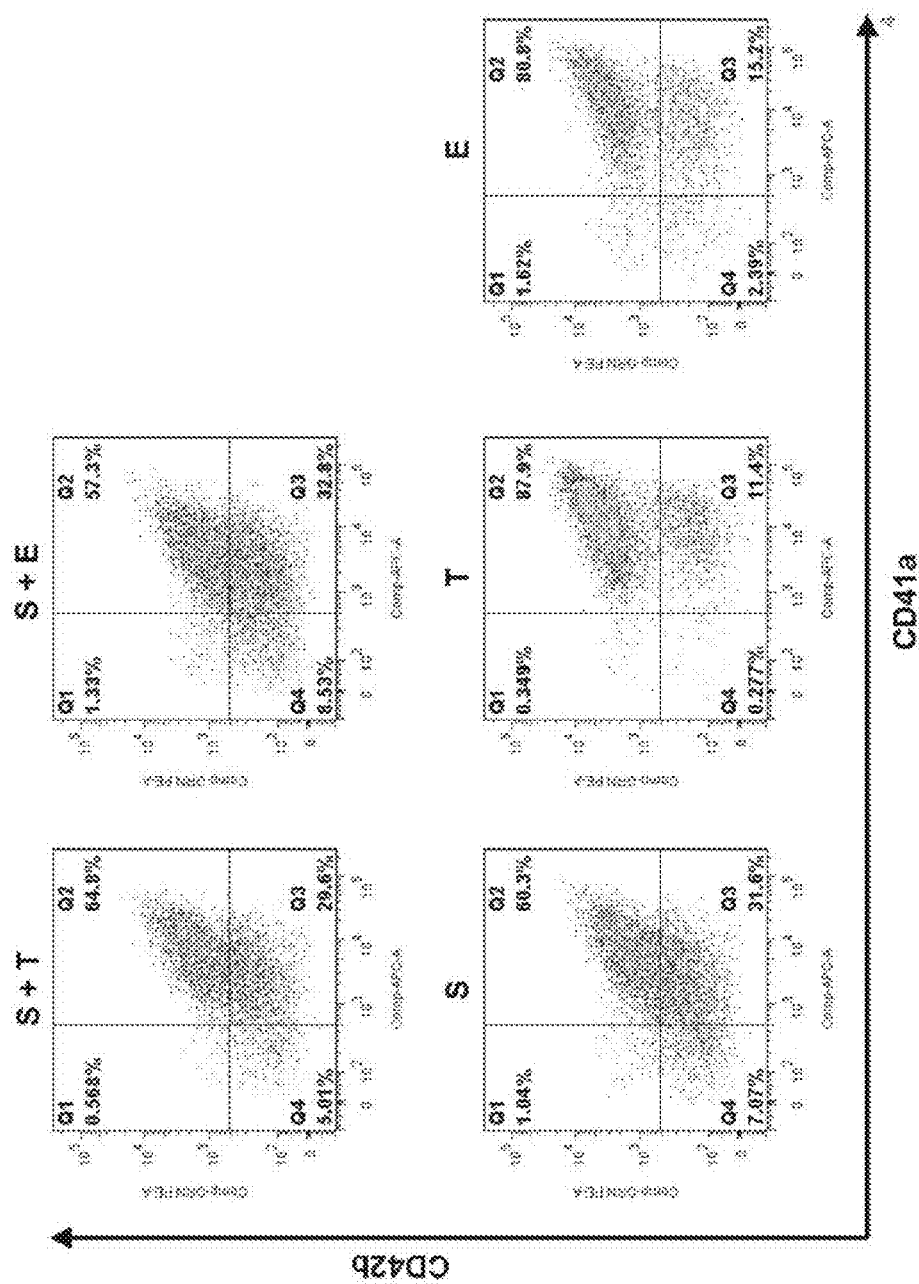
FIG. 1C It shows flow cytometry histograms of the expression of a surface marker of iMKPC-type I on Day 8 of the schedule shown in FIG. 1A.

The results are shown in FIGS. 1B and C. As shown in FIG. 1B, proliferation of iMKPC-type I cells strongly depended on SCF. As shown in FIG. 1C, the cells of any population were almost CD41 positive, but in the populations without SCF, the CD41+/CD42b− population showed a marked reduction in proliferation. The CD41+/CD42b− population is a population showing good proliferation among the iMKPC-type I cells.

These findings including SCF dependent proliferation suggest that iMKPC-type I cells are immature megakaryocytes.

1-2. Preparation of Megakaryocytes Before Polyploidization from CD34-Positive Cells Derived from Cord Blood It was confirmed that megakaryocytes before polyploidization can be prepared from CD34-positive cells derived from the cord blood in a similar manner to that using ES cells or iPS cells.

More specifically, CD34-positive cells derived from the cord blood were infected three times with pMx-c-MYC and DNsam BMI1 viruses (each, retrovirus vector) at MOI=10 and the number of CD41a (megakaryocyte marker) positive cells on Day 14 and Day 21 was counted using FACS. Mock (Empty vector) was used as a control.

Figure 1D:
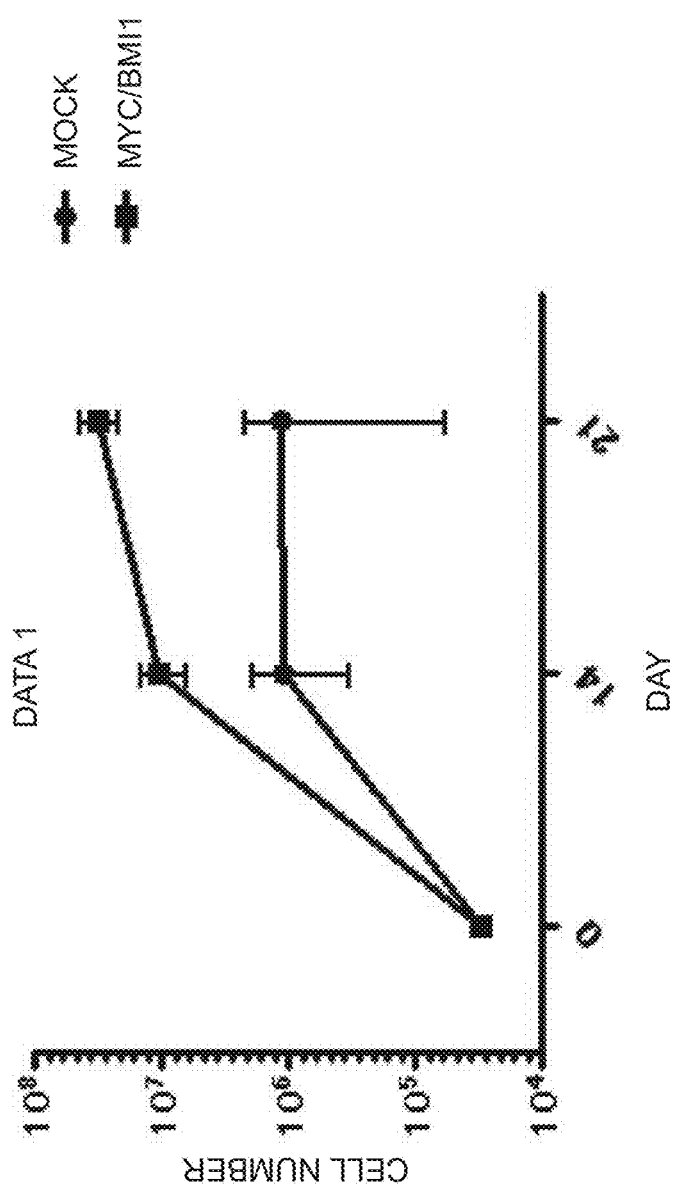
FIG. 1D It shows the results of forcing expression of c-MYC and BMI1 with CD34-positive cells derived from the cord blood and promoting proliferation of megakaryocytes before polyploidization.

The results are shown in FIG. 1D. Compared with Mock, proliferation of CD41 positive megakaryocytes was observed from a population in which c-MYC and BMI1 had been forcibly expressed. It was therefore confirmed that megakaryocytes before polyploidization can be obtained from cells derived from the cord blood in a similar manner to that described in 1-1.

2. Preparation of Polyploidized Megakaryocyte from Megakaryocytes Before Polyploidization 2-1. Influence of BCL-XL Expression on Polyploidization On Day 23 after infection with a pMx tet off c-MYC 2A BMI1 retrovirus vector containing c-MYC-2A-BMI1 in Section 1-1, the cells were infected once with doxycycline-inducible Lv-BCL-XL-GFP (lentivirus vector) at MOI=10. The vector was prepared by introducing PCR-amplified cDNA of BCL-XL into an Ai-Lv tet on vector (clontech) treated with EcoRI and BamHI by using an In-Fusion advance PCR cloning kit (clontech). Twenty four hours after infection, the virus was removed. By removing estradiol and adding Doxycyline, expression of c-MYC and BMI1 was suppressed and at the same time, expression of BCL-XL was started.

2-2. Influence of Knock Down of p53 Gene on Polyploidization

A p53 gene was knocked down by infecting it with a FG12-sh p53 lentivirus vector in addition to doxycycline-inducible Lv-BCL-XL-GFP lentivirus vector. The cells thus obtained may hereinafter be called "iMKPC-type II" cells.

2-3. Cytokine Dependence of iMKPC-Type II

Figure 2A:
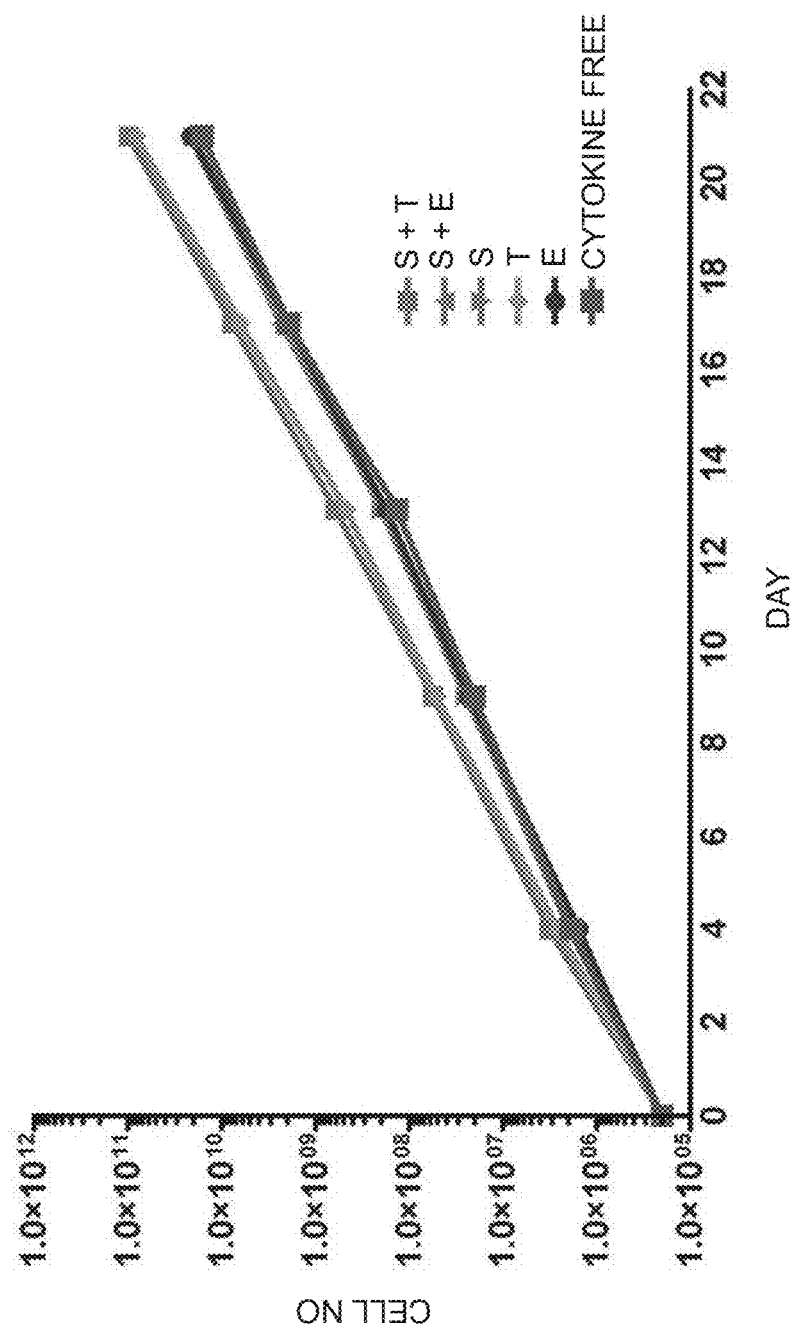
FIG. 2A It shows the results of studying the influence of cytokine on proliferation of iMKPC-type II.

On 10T1/2 feeder cells, $2\times10^5$ iMKPC-type II cells were seeded, followed by culturing in the presence of 0.5 μg/ml of Dox at 39° C. for 21 days under the conditions of cytokines, that is, SCF (50 ng/ml), TPO (50 ng/ml), and EPO (6 U/ml). The results are shown in FIG. 2A. It was confirmed that the iMKPC-type II cell line shows proliferation in the absence of cytokine, but proliferation is promoted further by the addition of TPO. Although the iMKPC-type I cells were SCF-dependent and TPO had no influence on their proliferation, the type II cells showed enhanced proliferation in the presence of TPO and SCF had no influence on proliferation.

2-4. Analysis of Surface Marker of iMKPC-Type II

Figure 2B:
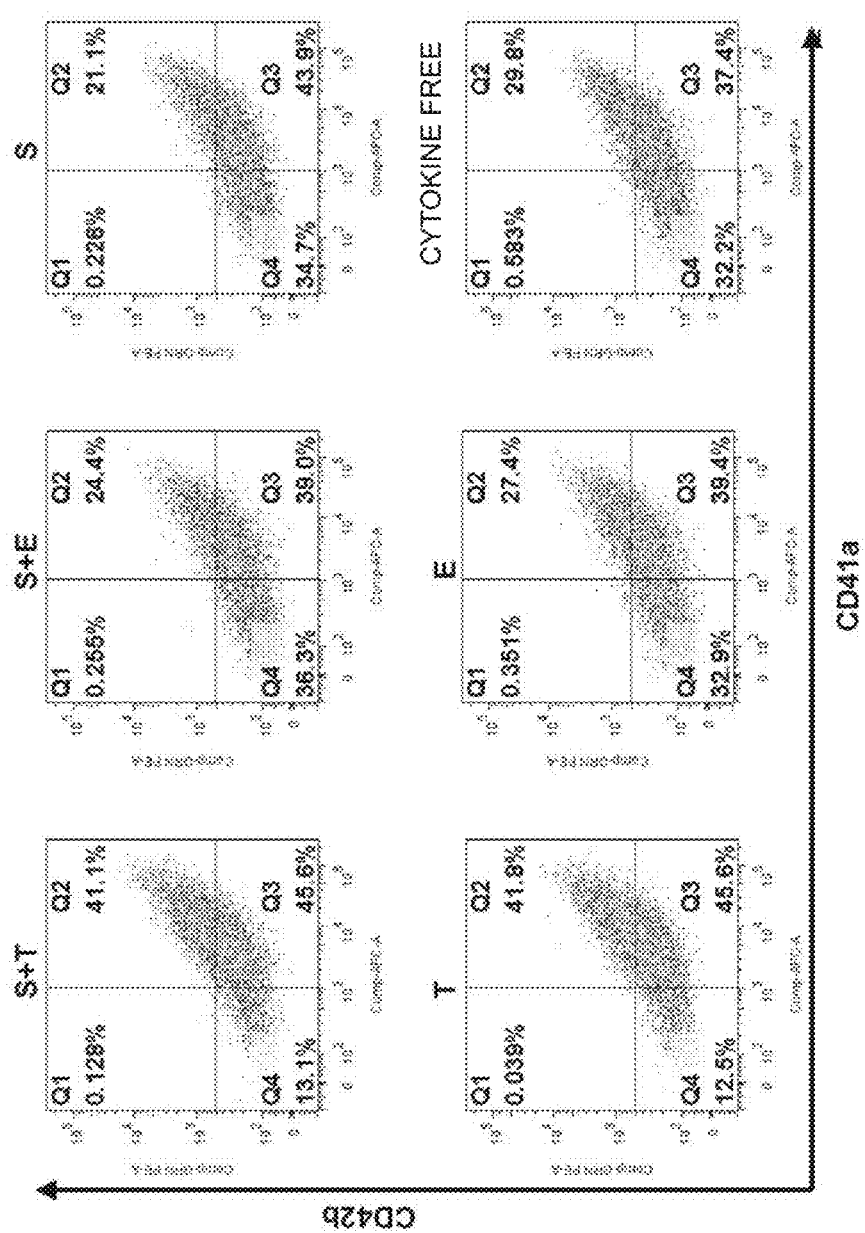
FIG. 2B It shows the results of studying the expression of CD41a and CD42b in iMKPC-type II.

On Day 21 after addition of cytokine, the cells were analyzed with a flow cytometer after staining with a CD41 antibody, a CD42b body, and a GPA antibody. The results are shown in FIG. 2B. The TPO-added population showed higher expression in CD41a and CD42b compared with the other populations, which suggests that it is a population further committed to megakaryocytes.

2-5. Morphological Change and Influence of Blebbistatin

Figure 3:
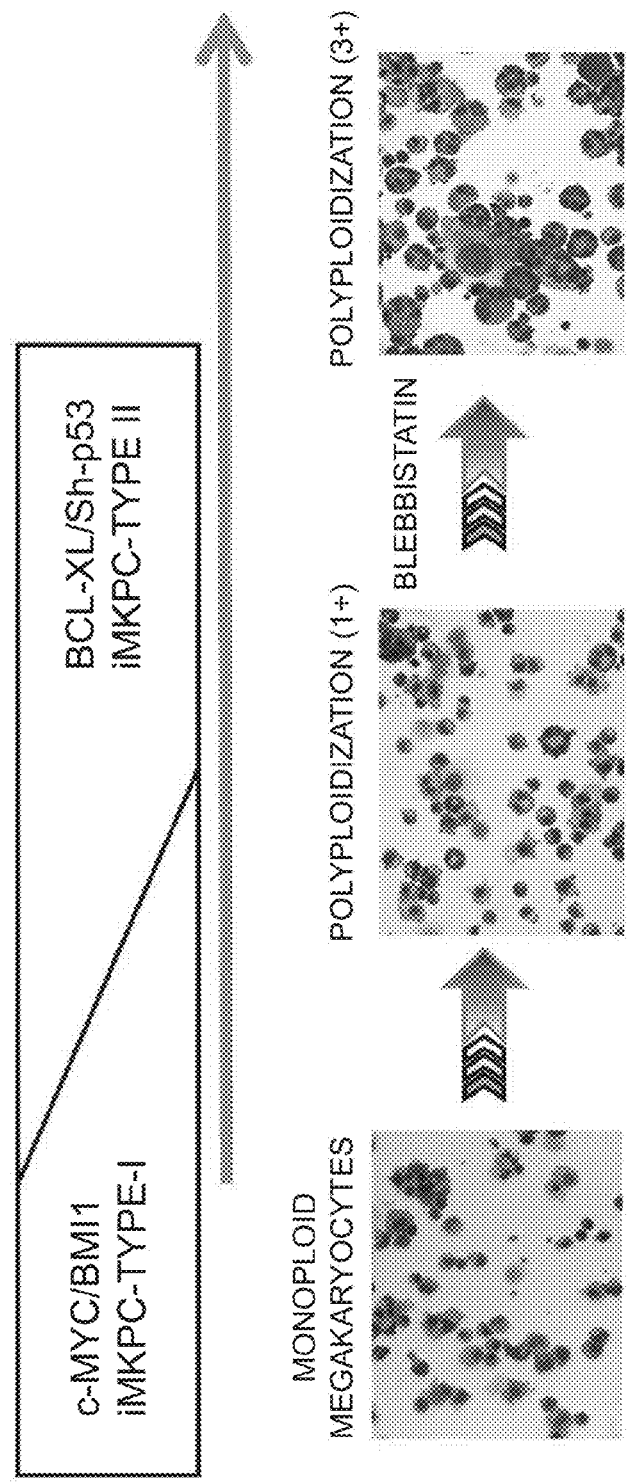
FIG. 3 It shows microscopic observations of polyploidization of iMKPC-type II when forced expression of BCL-XL and suppression of expression of a p53 gene were conducted, and of polyploidization when blebbistatin was added to the medium.

Microscopic observation results of iMKPC-type I and type II are shown in FIG. 3. It was observed that by turning off the expression of c-MYC and BMI1, forcing expression of BCL-XL, and knocking down the p53 gene, the cells become increasingly polyploidized. It was also confirmed that the cells were polyploidized further by the addition of blebbistatin (5 μg/ml).

As shown in Sections 2-3 to 2-5, in the stage of iMKPC-type II, megakaryocytes proliferate, a ratio of CD42b positive platelets in all the released platelets became higher, some of the cells were polyploidized, and cytokine dependence changed to TPO, suggesting that proliferation and maturation occurred in parallel to each other.

2-6. Influence of Suppression of BCL-XL Expression

On 10T1/2 feeder cells, $2\times10^5$ iMKPC-type II cells were seeded and long-term culture was conducted at 39° C. in the presence of 0.5 μg/ml of Dox (BCL-XL ON) or absence of it (BCL-XL OFF). Every two to five days, the number of cells was counted and $2\times10^5$ cells were replated.

Figure 4:
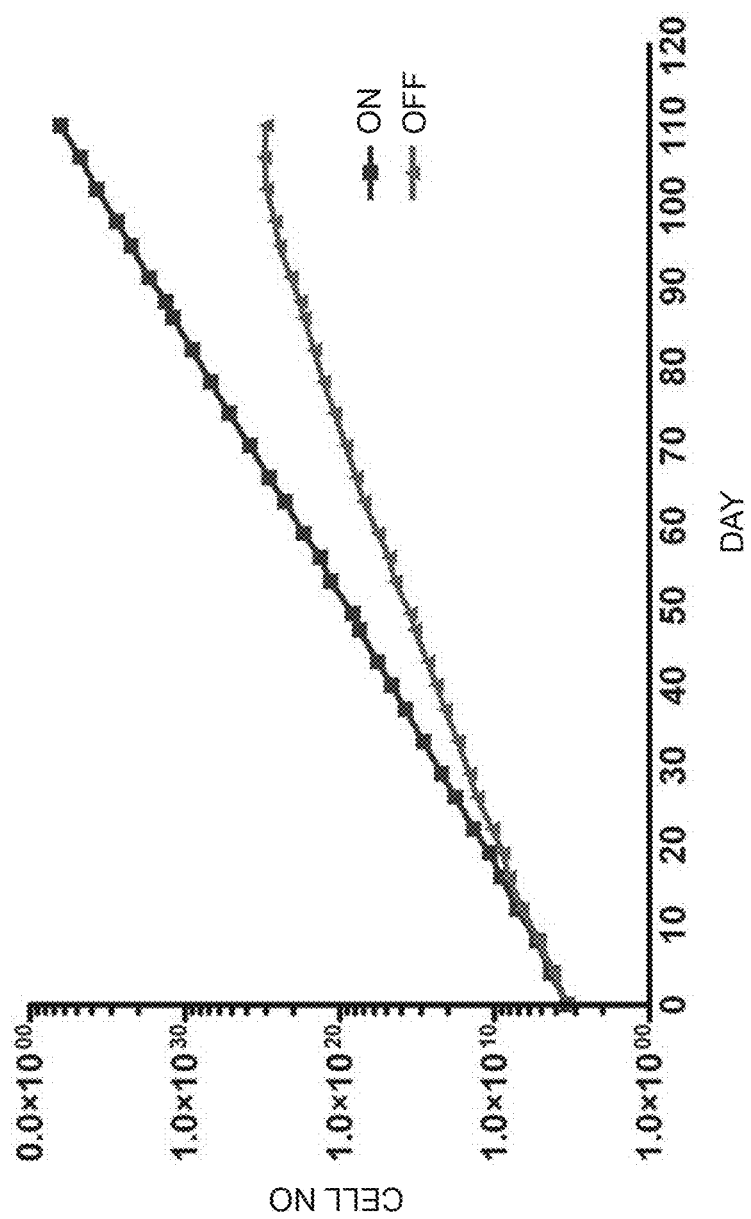
FIG. 4 It shows microscopic observations in the studying the influence of BCL-XL on proliferation of iMKPC-type II.

The results are shown in FIG. 4. Suppression of BCL-LX by Dox OFF decreased a proliferation rate of iMKPC-type II cells and after a long term (after 100 days), the cells lost their proliferation capacity, suggesting that BCL-XL is indispensable for long-term proliferation of iMKPC-type II cells.

Figure 5:
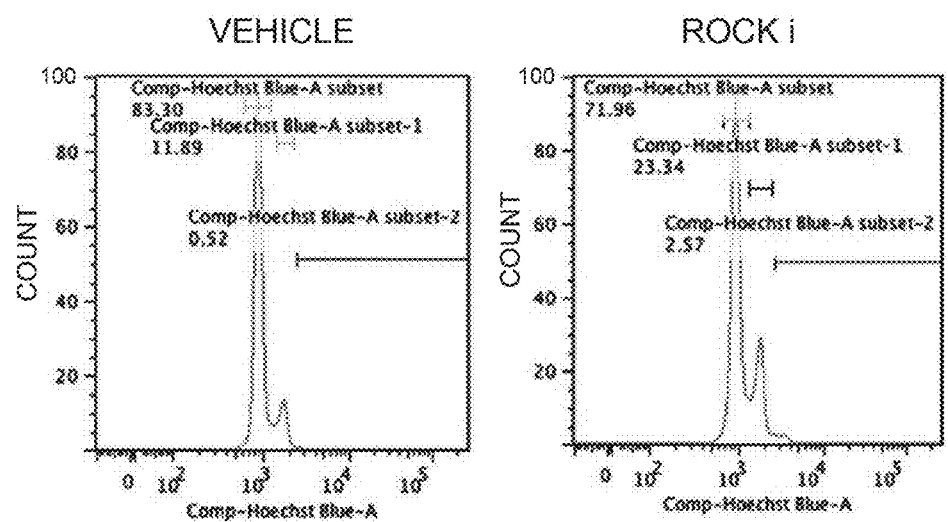
FIG. 5 Influence of an ROCK inhibitor on polyploidization of megakaryocytes. After expression of MYC/BMI1 in megakaryocytes was suppressed (by culturing in the presence of doxycycline and in the absence of estradiol), an ROCK inhibitor (Y27632) (10 μM) was added. After culturing for 7 days, the degree of polyploidization was studied. A shows flow cytometry histograms of cells (vehicle) to which the ROCK inhibitor had not been added and of cells (Rock i) to which the inhibitor had been added, wherein these cells were stained with Hoechst, a nuclear stain, then CD41a, a megakaryocyte marker was stained with an anti-CD41a antibody. B is a graph showing the results of A.
Figure 5:
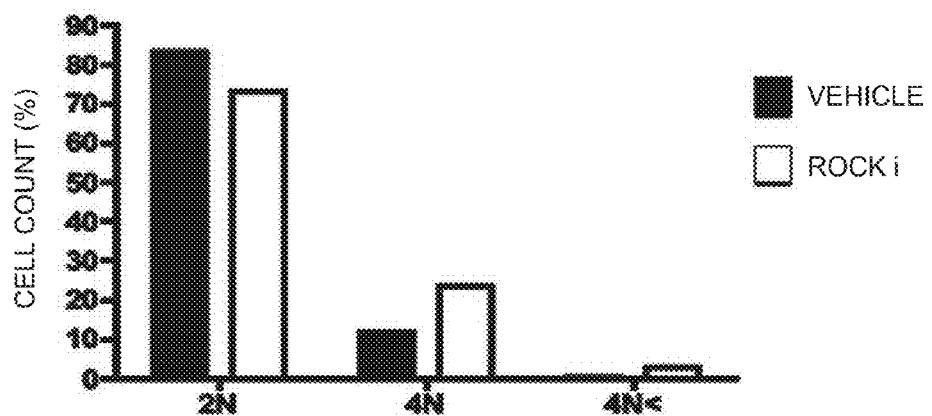

2-7. Study of the Influence of the Other Treatments on Polyploidization 2-7-1. Influence of ROCK Inhibitor After introduction of MYC and MBI1 genes, the resulting megakaryocytes (about $10^5$) were cultured for about 30 days in the absence of doxycycline and presence of estradiol under the culturing conditions of 37° C. and presence of 5% $CO_2$ to proliferate them to about $10^{11}$. Culturing was continued further while changing the condition to the presence of doxycycline and absence of estradiol in order to suppress the expression of the MYC gene and the BMI1 gene in the thus proliferated megakaryocytic cell line and adding an ROCK inhibitor (Y27632; product of Wako Pure Chemicals) to the culture medium to give a concentration of 10 μM in order to determine the influence of Y27632 on polyploidization. On Day 7 after culturing was started while adding Y27632 to the culture medium, the degree of polyploidization was studied using FACS (FIG. 5). The cells added with the ROCK inhibitor showed an increase in the number of cells with 4N (upper graph of FIG. 5 (Rock i), open square in the lower graph) compared with that in the cells added without the inhibitor (upper graph of FIG. 5 (vehicle), filled square). This revealed that the ROCK inhibitor promotes polyploidization of megakaryocytes before polyploidization which were derived from ES cells and acquired proliferation capacity as a result of expression of a C-MYC gene and a BMI1 gene.

2-7-2. Influence of ROCK Inhibitor+Culturing Under High-Temperature Condition

It has been reported to date that as a result of culturing immature megakaryocytes at a temperature, for example 39° C., higher than the normal culturing temperature, maturation of megakaryocytes is promoted, including polyploidization and proplatelet formation (Non-patent Document 5). In order to confirm this in megakaryocytes before polyploidization which have been derived from ES cells, an expression level of genes (GATA1, PF4, NFE2, and β-tubulin) known to show enhanced expression with maturation of megakaryocytes was studied using quantitative PCR.

Figure 6:
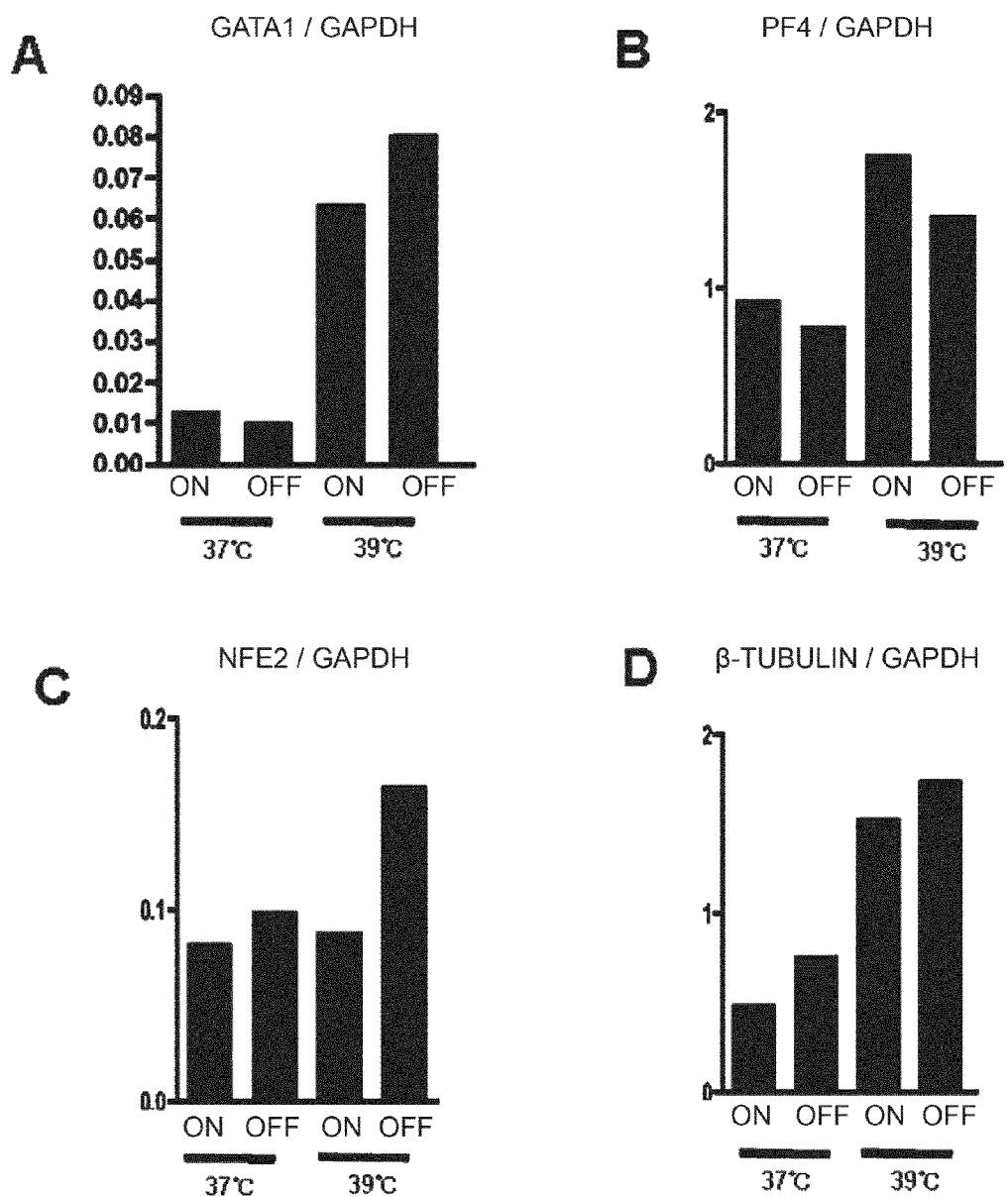
FIG. 6 Studying results of the expression level of a gene involved in maturation of megakaryocytes in culturing at 39° C. After expression of MYC/BMI1 in megakaryocytes was suppressed, the resulting cells were cultured at 39° C. for 5 days. The expression level of a gene group (GATA1 (A), PF4 (B), NFE2 (C), and β-tubulin (D)) indispensable for maturation of megakaryocytes was studied through quantitative PCR (q-PCR). The expression level shown in these graphs is a ratio to the expression level of GAPDH.

Proliferation of megakaryocytes before polyploidization was promoted. In order to suppress the expression of the MYC gene and BMI1 gene in the resulting megakaryocytes before polyploidization, culturing was conducted for 5 days under changed conditions, that is, in the presence of doxycycline and the absence of estradiol and at a culturing temperature of 39° C. Then, quantitative PCR was conducted to measure the expression level of the respective genes (FIG. 6). As a result, it was found that the expression levels of the genes serving as an indicator of maturation of megakaryocytes were greater in culturing at 39° C. than in culturing at 37° C.

2-7-3. Influence of ROCK Inhibitor+Forced Expression of BCL-XL Gene

Expression of MYC/BMI1 in megakaryocytes before polyploidization was suppressed and at the same time, a lentivirus vector similar to that used in 2-1 for inducing expression of BCL-XL was introduced into the cells in the presence of doxycycline.

Figure 7:
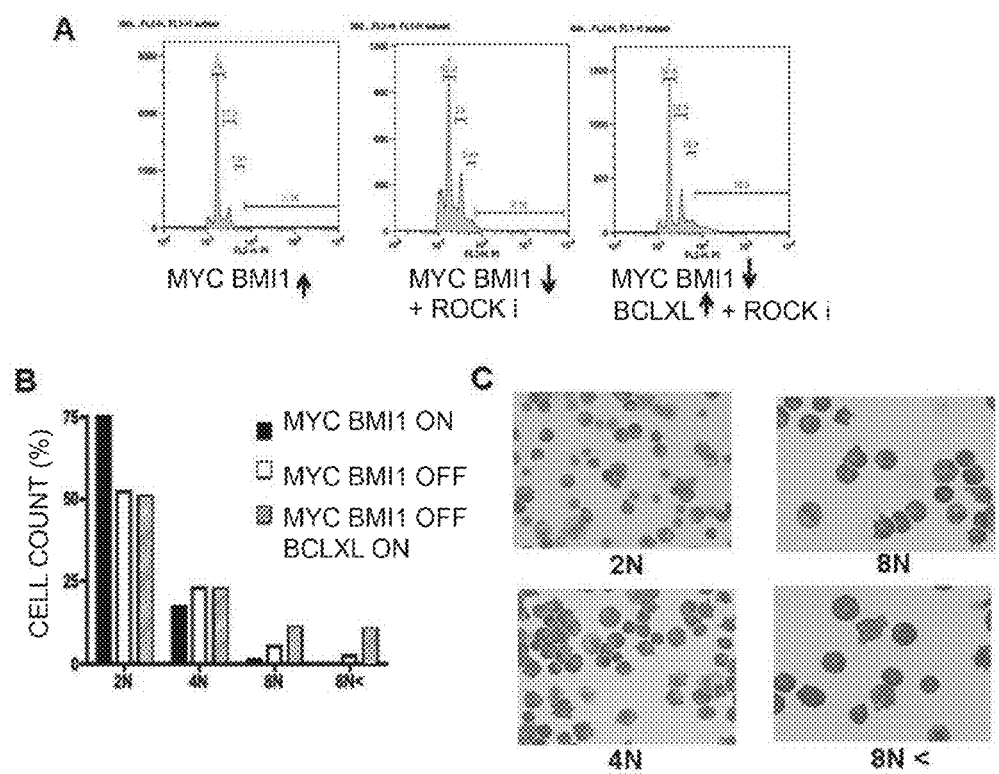
FIG. 7 Studying results of the influence of BCL-XL, one of apoptosis suppressor genes, on polyploidization of megakaryocytes. The degree of polyploidization was studied after suppressing expression of MYC/BMI1 in megakaryocytes, inducing expression of BCL-XL in the presence of an ROCK inhibitor (10 μM), and culturing the resulting cells for 7 days. A shows flow cytometry histograms of each of MYC/BMI1 expressed cells (left graph), of cells treated with an ROCK inhibitor after suppression of MYC/BMI1 expression (middle graph), and of cells subjected to expression of BCL-XL in addition to suppression of expression of MYC/BMI1 and treatment with an ROCK inhibitor (right graph), wherein these cells were stained with a nuclear stain, Hoechst, and then CD41a, a megakaryocyte marker, was stained with an anti-CD41a antibody. B is a graph showing the results of A. C includes micrographs of cells having a nucleus of 2N, 4N, 8N, and 8N or greater.

It was studied if polyploidization of megakaryocytic progenitor cells derived from an ROCK inhibitor by the presence or absence of expression of a BCL-XL gene (FIG. 7).

Figure 8:
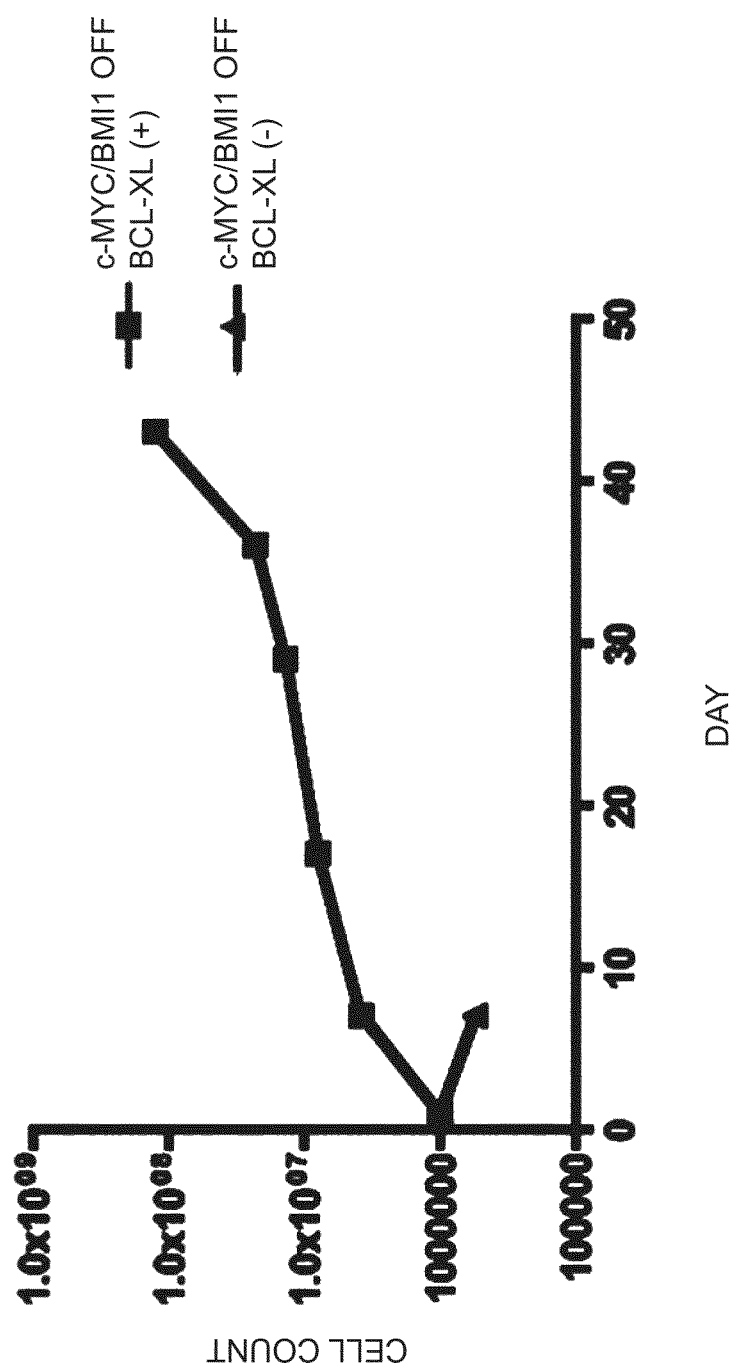
FIG. 8 Growth curve of BCL-XL expressed cells. It shows the results of a change in the number of BCL-XL expressed cells (CD41a+) (■) and the number of non-expressed cells (CD41a+) (▲) as a function of culturing days while suppressing expression of MYC/BMI1 in megakaryocytes in the presence of an ROCK inhibitor (10 μM).

The degree of polyploidization was studied (ploidy assay) by suppressing expression of MYC/BMI1 in the presence of 10 μM of Y27632 while inducing suppression of BCL-XL, and culturing the resulting cells for 7 days. It was confirmed that the number of polyploidized cells with 8N or greater significantly increased in the BCL-XL expressed cell line (a shaded bar in FIG. 7B) compared with a cell line (a blank bar in FIG. 7B) in which BCL-XL was not expressed. In addition, it was observed that the number of the cells in which BCL-XL was expressed showed a gradual increase (■ in FIG. 8) while the number of the cells in which BCL-XL was expressed decreases (▲ in FIG. 8).

This suggests that in order to avoid oncogene dependence in megakaryocytes before polyploidization which acquired high proliferation capacity as a result of forced expression of the oncogene, genes suppressing apoptosis such as BCL-XL gene were effective.

2-7-4. Influence of ROCK Inhibitor+Forced Expression of BCL-XL Gene+Suppression of p53 Gene It was studied whether suppression of expression of p53 promoted polyploidization of megakaryocytes before polyploidization or not.

Expression of the p53 gene was suppressed as in 2-2 by lentivirus infection at MOI=10 by using a lentivirus FG12 vector in which one promoter, shp53 had been introduced.

Figure 9:
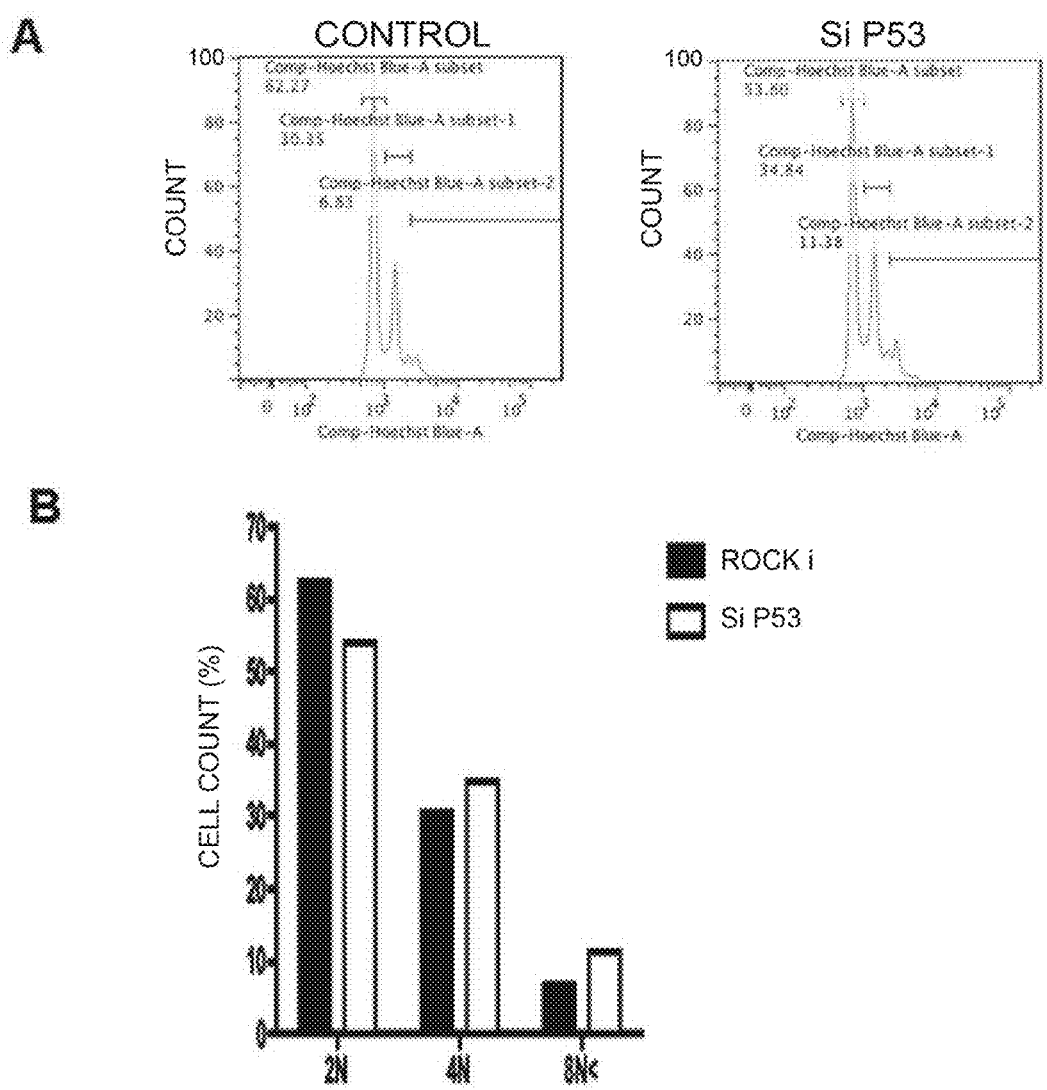
FIG. 9 Influence of p53 knockdown on polyploidization. The degree of polyploidization of CD41a+ cells was studied by suppressing expression of MYC/BMI1 in megakaryocytes, inducing expression of BCL-XL in the presence of an ROCK inhibitor (10 μM), knocking down a p53 gene, and then culturing the resulting cells at 39° C. for 7 days. A shows flow cytometry histograms of each of control cells (control) in which p53 had not been knocked down and of cells (SiP53) in which p53 had been knocked down, wherein these cells were stained with a nuclear stain Hoechst, and then CD41a, a megakaryocyte marker was stained with an anti-CD41a antibody. B is a graph showing the results of A.

After suppression of expression of MYC/BMI1, forced expression of BCL-XL, and suppression of expression of p53 in the presence of Y27632, culturing was conducted for 7 days at 39° C. After culturing, the degree of polyploidization was studied. As a result, it was found that compared with control cells (black bar in FIG. 9B) in which p53 was not knocked down, cells (blank bar in FIG. 9B) in which p53 was knocked down showed an increase in the number of the cells with 8N and polyploidization was promoted.

Figure 10:
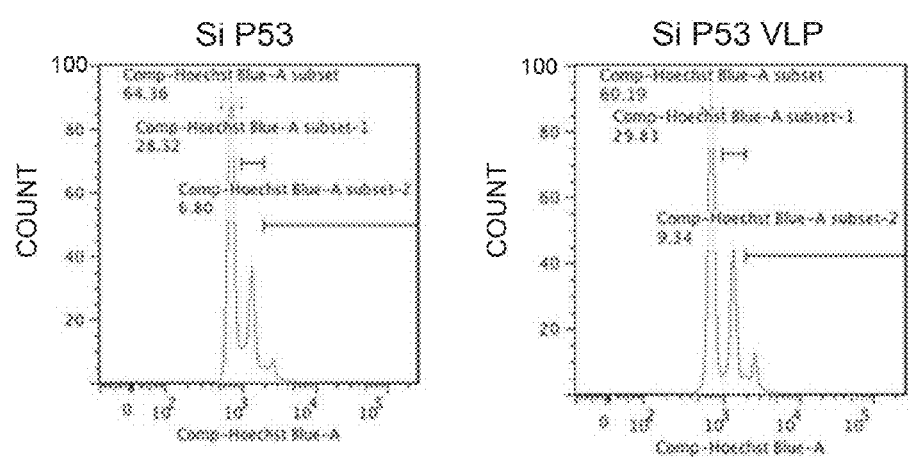
FIG. 10 Influence of valproic acid treatment on polyploidization. The degree of polyploidization of CD41a+ cells was studied after suppressing the expression of MYC/BMI1 in megakaryocytes, inducing expression of BCL-XL in the presence of an ROCK inhibitor (10 μM), knocking down a p53 gene, treating the resulting cells with valproic acid (0.5 mM), and culturing at 39° C. for 7 days. A shows flow cytometry histograms of each of cells (Si P53) not treated with valproic acid and of cells (SiP53 VLP) treated with valproic acid, wherein these cells were stained with a nuclear stain Hoechst, and then CD41a, a megakaryocyte marker was stained with an anti-CD41a antibody. B is a graph showing the results of A.
Figure 10:
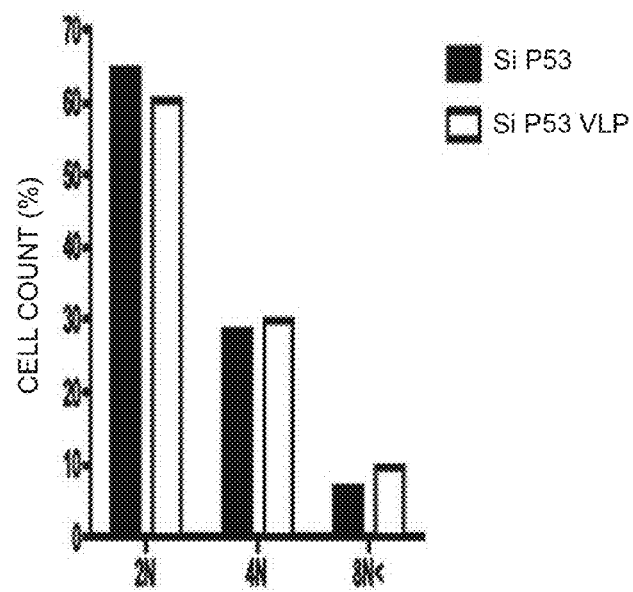

2-7-5. Influence of ROCK Inhibitor+Forced Expression of BCL-XL Gene+Suppression of p53 Gene+Valproic Acid Influence on polyploidization was studied by further treating the cells, which was subjected to the treatment of 2-7-4, with valproic acid. After suppression of expression of MYC/BMI1, forced expression of BCL-XL, treatment with the ROCK inhibitor (10 μM), and suppression of expression of p53, valproic acid (final concentration: 0.5 mM) was added to the medium and culturing was conducted at 39° C. for 7 days. As a result, it was found that cells (blank bar in FIG. 10B) treated with valproic acid showed promoted polyploidization compared with control cells (black bar in FIG. 10B) which was not subjected to valproic acid treatment.

2-7-6. Influence of Forced Expression of BCL-XL Gene+Myosin Heavy Chain IIA/B ATPase Inhibitor and Influence of ROCK Inhibitor+Forced Expression of BCL-XL Gene+Suppression of p53 Gene+Valproic Acid+Myosin Heavy Chain IIA/B ATPase Inhibitor It was studied whether treatment of megakaryocytes the polyploidization of which have not proceeded sufficiently with blebbistatin, that is, a myosin heavy chain IIA/B ATPase inhibitor had an influence on the degree of polyploidization. After suppression of expression of MYC/BMI1, forced expression of BCL-XL, and treatment with blebbistatin (10 μg/ml), the resulting cells were cultured at 39° C. for 7 days. It was found that the number of cells with 8N or greater was greater in the cells subjected to blebbistatin treatment (blank bar in FIG. 11) than in the cells not subjected to blebbistatin treatment (black bar in FIG. 11*b*), showing promoted polyploidization.

Next, the degree of polyploidization when the blebbistatin treatment was used in combination with the other treatments was studied. The cells were subjected to blebbistatin treatment in addition to the above-mentioned treatments in Section 2-7-5 and influence of them on polyploidization was studied. After suppression of expression of MYC/BMI1, forced expression of BCL-XL, treatment with a ROCK inhibitor (10 μM), suppression of expression of p53, and treatment with valproic acid (0.5 mM), treatment with blebbistatin (10 μg/ml) was conducted and then, the resulting cells were cultured at 39° C. for 7 days. It was found that the number of cells with 8N or greater was greater in the cells subjected to blebbistatin treatment (blank bar in FIG. 12) than in the control cells not subjected to blebbistatin treatment (black bar in FIG. 12*b*), showing that the treatments promoted polyploidization. In addition, after culturing for 7 days, the cells treated with blebbistatin showed a slight deterioration in proliferation capacity (upper graph in FIG. 13) but hypertrophy of cytoplasm was observed. Induction to mature megakaryocytes was therefore confirmed (lower graph in FIG. 13).

3. Production of Platelets from Polyploidized Megakaryocytes 3-1. Influence of Suppression of Expression of BCL-XL on Platelet Production (1)

On 10T1/2 feeder cells, $2\times10^5$ iMKPC-type II cells obtained in Section 2-2 were seeded, followed by culturing at 39° C. in the presence of 0.5 μg/ml of Dox (BCL-XL ON) or after removal of Dox from the culture medium (BCL-XL OFF). On Day 3-4, the megakaryocytes and the platelets in the culture medium were analyzed with a flow cytometer after a staining with a CD41 antibody and a CD42 antibody.

The results are shown in FIG. 14. It was found that the population (B) in which expression of BclxL was suppressed by Dox OFF becomes composed mainly of mature megakaryocytes in which CD42b was expressed (B) compared with the megakaryocytes (A) in which BCL-XL was expressed by Dox ON. It was also found that with regard to the platelets released from them, a ratio of the platelets in which CD42b necessary for function expression was expressed became greater (D) than that of the platelets (C) released from the megakaryocytes of BCL-XL ON.

3-2. Influence of Suppression of Expression of BCL-XL on Platelet Production (2)

FIG. 15 shows the measurement results of the number of cells when BCL-XL expression was ON or OFF, based on the results similar to those shown in Section 3-1. The number of platelets became markedly greater in the population in which expression of BCL-XL has been suppressed.

A shows the number of CD42b-positive platelets; B shows the number of CD41a-positive/CD42b-positive megakaryocytes, and C shows the number of CD41a-positive megakaryocytes.

No influence of BclxL expression on the number of megakaryocytes in which CD41 was expressed could be found (C), but it was presumed that an expression ratio of CD42b in CD41+ increased due to suppression of expression of BclxL and the number of mature megakaryocytes increased.

3-3. Influence of Culturing Temperature on Platelet Production

On 10T1/2 feeder cells, from 2 to $3\times10^5$ iMKPC-type II cells were seeded and cultured for 3 days at culturing temperatures of 35, 37, and 39° C. while adding or not adding 0.5 μg/mL of Dox. The platelets contained in the supernatant were analyzed with a flow cytometer after staining with a CD41 antibody and a CD42b antibody. With 37° C. Dox+ as 1, the mean and standard deviation of the number of CD41+ CD42b+ platelets of each population are shown in FIG. 16.

It was found from the results that the culturing temperature of 37° C. or 39° C. is adequate. In the tests conducted later, the culturing temperature was set at 37° C.

3-4. Influence of Feeder Cells, Use of Serum for Culture, and Presence or Absence of Blebbistatin on Platelet Production A platelet production efficiency was measured by using the following conditions in combination as shown in FIG. 17: use/non-use of feeder cells, use/non-use of Conditioned Medium, use of serum medium/use of serum-free medium, and administration/non-administration of blebbistatin.

Conditioned Medium was prepared by seeding $8\times10^5$ MMC-treated 10T1/2 cells on a 10-cm dish subjected to gelatin coating, changing the medium with 10 ml of a differentiation medium (EBM) containing SCF (50 ng/ml) and TPO (50 ng/ml) and further containing 15% serum or not containing a serum on the next day (after adhesion of cells), recovering the medium and adding 10 ml of a new medium (containing SCF and TPO) 24 hours later, pooling three-day's Conditioned Medium, and filtering the medium through a 0.22-μm filter to remove the 10T1/2 cells. When the resulting medium was used for tests, SCF and TPO were added newly.

In a feeder cell using population, from 2 to $3\times10^5$ iMKPC-type II cells were seeded on 10T1/2 feeder cells, while in the non-use population, the cells were seeded on a gelatin-coated dish similarly. In the serum medium using population, a 15% serum-containing differentiation medium or Conditioned Medium was used, while in the blebbistatin administration population, 5 μM of blebbistatin was added to the medium. Culturing was conducted at 37° C. for 3 days.

The platelets contained in the supernatant of the medium were analyzed with a flow cytometer after staining with an antibody CD41 and an antibody CD42b. With the cells obtained by culturing on feeder cells while adding 15% serum without adding blebbistatin as normal condition cells, the mean and standard deviation of a ratio of the number of CD41+ CD42b+ platelets in each population with respect to those of the normal condition are shown in bar graph in FIG. 17. No significant difference in the platelet production amount was found among the populations.

Comparison in the expression level of CD42b in CD41-positive platelets in each population (a ratio of average fluorescence intensity of each population to average fluorescence intensity of normal condition) is shown in FIG. 18. Under serum-free and feeder cell-free conditions, the platelets showing the highest CD42b expression were produced. Influence of blebbistatin was not found.

One example of the optimized conditions is shown in FIG. 19. A ratio of CD41-positive and CD42b (which may be called "GPIba")-positive platelets when cultured under the optimized conditions is shown in FIG. 20.

As shown in FIG. 20, in the platelets produced from the polyploidized megakaryocytes obtained by the present invention, about 20% were CD41-positive and CD42b positive. When expression of BCL-XL was suppressed, the ratio increased to 55% and when culturing was conducted while removing the feeder cells and the serum in addition, the ratio increased even to 81%.

4. Importance of CD42b Expression for Platelet Function (Reference)

An inhibitory effect of an HIP1 antibody on a ristocetin agglutination reaction (agglutination reaction via vWF and a receptor [hetero pentamer composed of GPIba, GPIX, and the like] on platelets) was measured using human peripheral blood platelets. The HIP1 antibody was a function inhibiting antibody of GPIba.

After the effect of GPIba was inhibited by suspending $1\times10^8$ platelets in 50% blood plasma, adding an HIP1 antibody thereto, and pre-culturing at 37° C. for 3 seconds, ristocetin (final concentration: 2 mg/ml) was added to induce an agglutination reaction and light transmission was monitored for 7 minutes. The maximum light transmission (showing agglutination intensity) of each population is shown in bar graph in FIG. 21. The HPI1 antibody completely inhibited agglutination due to GPIb/alpha-von Willebrand factor (vWF) association at a concentration of 10 μg/ml or greater.

Next, 100 ug of an HIP1 antibody or control IgG was administered into NOG mice and platelets stained with-TAMRA (red dye) were transplanted. The vascular endothelium was exposed to laser to damage it and induce thrombus formation. The number of human platelets (red) which had contributed to the thrombus formation was counted.

The mean and standard deviation of the number of human platelets in the thrombi corrected with a unit blood vessel length are shown in bar graph (FIG. 22). In the HIP1 antibody administered group, contribution of human platelets to thrombus was inhibited.

It was therefore found that GPIba (CD42b) is a molecule playing an important role in thrombus formation both in vivo and in vitro.

INDUSTRIAL APPLICABILITY

The present invention provides a method of promoting polyploidization of megakaryocytic progenitor cells and moreover, efficiently inducing release of platelets. In particular, the method of the present invention is very effective for the preparation of megakaryocytes or platelets in vitro from various stem cells and it greatly contributes to the development of remedies in medical fields or blood products.

The invention claimed is:

1. A method of producing polyploidized megakaryocytes, comprising:
  inducing expression of an apoptosis suppressor gene, a MYC family gene, and a BMI1 gene in megakaryocytes before polyploidization, and
  culturing the resulting cells from the inducing step, wherein the oncogene is different from the apoptosis suppressor gene.

2. The method according to claim 1, wherein the apoptosis suppressor gene is a BCL-XL gene.

3. The method according to claim 1, wherein the culturing step comprises inhibiting expression or function of a p53 gene product.

4. The method according to claim 1, wherein the megakaryocytes before polyploidization are subjected to at least one of the following (a) to (c):
  (a) treatment with an actomyosin complex function inhibitor;
  (b) treatment with an Rho-associated coiled-coil forming kinase/Rho associated kinase (ROCK) inhibitor; and (c) treatment with an Histone deacetylase (HDAC) inhibitor.

5. The method according to claim 4, wherein the ROCK inhibitor is [(R)-(+)-trans-N-(4-pyridyl)-4-(1-aminoethyl)-cyclohexane carboxamide. 2HCl. $H_2O$] (Y27632); the HDAC inhibitor is valproic acid; and the actomyosin complex function inhibitor is blebbistatin.

6. The method according to claim 1, wherein the culturing step is conducted at a temperature higher than 37° C.

7. The method according to claim 1, wherein the MYC family gene is a c-MYC gene.

8. The method according to claim 1, wherein the megakaryocytes before polyploidization are derived from cells selected from the group consisting of induced pluripotent stem (iPS) cells, embryonic stem (ES) cells, hematopoietic stem cells derived from cord blood, bone marrow blood, peripheral blood, and hematopoietic stem cells.

9. A method of producing platelets, comprising:
obtaining polyploidized megakaryocytes by the method according to claim 1,
culturing the polyploidized megakaryocytes to produce culture of the polyploidized megakaryocytes; and
collecting the platelets from the culture of the polyploidized megakaryocytes.

10. The method according to claim 9, wherein the step of culturing the polyploidized megakaryocytes is conducted while suppressing the expression of the apoptosis suppressor gene that has been induced, or after the apoptosis suppressor gene is removed from the cells.

11. The method according to claim 9, wherein the step of culturing the polyploidized megakaryocytes is conducted in the absence of serum and/or in the absence of a feeder cell.

12. The method according to claim 9, wherein the step of culturing the polyploidized megakaryocytes is conducted from 1 day to 15 days.

13. The method according to claim 9, wherein the step of culturing the polyploidized megakaryocytes is conducted at 37° C.

14. The method according to claim 9, wherein in the step of culturing the polyploidized megakaryocytes, an ROCK inhibitor and/or an actomyosin complex function inhibitor is added to a medium.

15. The method according to claim 14, wherein the ROCK inhibitor is Y27632, and the actomyosin complex function inhibitor is blebbistatin.

16. The method according to claim 1, further comprising treating the megakaryocytes before polyploidization with one or more inhibitors selected from the group consisting of an actomyosin complex function inhibitor; an Rho-associated coiled-coil forming kinase/Rho associated kinase (ROCK) inhibitor; and an Histone deacetylase (HDAC) inhibitor.

17. The method according to claim 9, wherein the method comprises treating the megakaryocytes before polyploidization with the Rho-associated coiled-coil forming kinase/Rho associated kinase (ROCK) inhibitor.

\* \* \* \* \*

SEQUENCE LISTING

<160> NUMBER OF SEQ ID NOS: 3

<210> SEQ ID NO 1
<211> LENGTH: 1319
<212> TYPE: DNA
<213> ORGANISM: Homo sapiens

<400> SEQUENCE: 1

```
atgcccctca acgttagctt caccaacagg aactatgacc tcgactacga ctcggtgcag      60
ccgtatttct actgcgacga ggaggagaac ttctaccagc agcagcagca gagcgagctg     120
cagcccccgg cgcccagcga ggatatctgg aagaaattcg agctgctgcc caccccgccc     180
ctgtccccta gccgccgctc cgggctctgc tcgccctcct acgttgcggt cacacccttc     240
tcccttcggg gagacaacga cggcggtggc gggagcttct ccacggccga ccagctggag     300
atggtgaccg agctgctggg aggagacatg gtgaaccaga gtttcatctg cgacccggac     360
gacgagacct tcatcaaaaa catcatcatc caggactgta tgtggagcgg cttctcggcc     420
gccgccaagc tcgtctcaga gaagctggcc tcctaccagg ctgcgcgcaa agacagcggc     480
agcccgaacc ccgcccgcgg ccacagcgtc tgctccacct ccagcttgta cctgcaggat     540
ctgagcgccc ccgctcagag tgcatcgacc cctcggtggt cttccccctac cctctcaacg     600 acagcagctc gcccaagtcc tgcgcctcgc aagactccag cgccttctct ccgtcctcgg     660
attctctgct ctcctcgacg gagtcctccc cgcagggcag ccccgagccc ctggtgctcc     720
atgaggagac accgcccacc accagcagcg actctgagga ggaacaagaa gatgaggaag     780
aaatcgatgt tgtttctgtg gaaagaggc aggctcctgg caaaaggtca gagtctggat     840
caccttctgc tggaggccac agcaaacctc ctcacagccc actggtcctc aagaggtgcc     900
acgtctccac acatcagcac aactacgcag cgcctccctc cactcggaag gactatcctg     960
ctgccaagag ggtcaagttg gacagtgtca gagtcctgag acagatcagc aacaaccgaa    1020
aatgcaccag ccccaggtcc tcggacaccg aggagaatgt caagaggcga acacacaacg    1080
tcttggagcg ccagaggagg aacgagctaa acggagctt ttttgccctg cgtgaccaga    1140
tcccggagtt ggaaaacaat gaaaaggccc ccaaggtagt tatccttaaa aaagccacag    1200
catacatcct gtccgtccaa gcagaggagc aaaagctcat ttctgaagag gacttgttgc    1260
ggaaacgacg agaacagttg aaacacaaac ttgaacagct acggaactct tgtgcgtaa     1319
```

<210> SEQ ID NO 2
<211> LENGTH: 981
<212> TYPE: DNA
<213> ORGANISM: Homo sapiens

<400> SEQUENCE: 2

```
atgcatcgaa caacgagaat caagatcact gagctaaatc cccacctgat gtgtgtgctt      60
```

```
tgtggagggt acttcattga tgccacaacc ataatagaat gtctacattc cttctgtaaa      120
acgtgtattg ttcgttacct ggagaccagc aagtattgtc ctatttgtga tgtccaagtt      180
cacaagacca gaccactact gaatataagg tcagataaaa ctctccaaga tattgtatac      240
aaattagttc cagggctttt caaaaatgaa atgaagagaa gaagggattt ttatgcagct      300
catccttctg ctgatgctgc caatggctct aatgaagata gaggagaggt tgcagatgaa      360
gataagagaa ttataactga tgatgagata ataagcttat ccattgaatt ctttgaccag      420
aacagattgg atcggaaagt aaacaaagac aaagagaaat ctaaggagga ggtgaatgat      480
aaaagatact tacgatgccc agcagcaatg actgtgatgc acttaagaaa gtttctcaga      540
agtaaaatgg acatacctaa tactttccag attgatgtca tgtatgagga ggaacccttta     600 aaggattatt atacactaat ggatattgcc tacatttata cctggagaag gaatggtcca      660
cttccattga aatacagagt tcgacctact tgtaaaagaa tgaagatcag tcaccagaga      720
gatggactga caaatgctgg agaactggaa agtgactctg ggagtgacaa ggccaacagc      780
ccagcaggag gtattccctc cacctcttct tgtttgccta gccccagtac tccagtgcag      840
tctcctcatc cacagtttcc tcacatttcc agtactatga atggaaccag caacagcccc      900
agcggtaacc accaatcttc ttttgccaat agacctcgaa aatcatcagt aaatgggtca      960
tcagcaactt cttctggttg a                                                981

<210> SEQ ID NO 3
<211> LENGTH: 702
<212> TYPE: DNA
<213> ORGANISM: Homo sapiens

<400> SEQUENCE: 3
atgtctcaga gcaaccggga gctggtggtt gactttctct cctacaagct ttcccagaaa       60
ggatacagct ggagtcagtt tagtgatgtg aagagaaca ggactgaggc cccagaaggg      120
actgaatcgg agatggagac ccccagtgcc atcaatggca acccatcctg gcacctggca      180
gacagccccg cggtgaatgg agccactggc cacagcagca gtttggatgc ccggaggtg       240 atccccatgg cagcagtaaa gcaagcgctg agggaggcag gcgacgagtt tgaactgcgg      300
taccggcggg cattcagtga cctgacatcc cagctccaca tcaccccagg gacagcatat      360
cagagctttg aacaggtagt gaatgaactc ttccgggatg gggtaaactg gggtcgcatt      420
gtggcctttt tctccttcgg cggggcactg tgcgtggaaa gcgtagacaa ggagatgcag      480
gtattggtga gtcggatcgc agcttggatg gccacttacc tgaatgacca cctagagcct      540
tggatccagg agaacggcgg ctgggatact tttgtggaac tctatgggaa caatgcagca      600
gccgagagcc gaaagggcca ggaacgcttc aaccgctggt tcctgacggg catgactgtg      660
gccggcgtgg ttctgctggg ctcactcttc agtcggaaat ga                         702
```